US009364291B2

(12) United States Patent
Bellettre et al.

(10) Patent No.: US 9,364,291 B2
(45) Date of Patent: Jun. 14, 2016

(54) IMPLANT PLANNING USING AREAS REPRESENTING CARTILAGE

(75) Inventors: Alexandra Bellettre, Salt Lake City, UT (US); Louis Arata, Mentor, OH (US); Robert Van Vorhis, Davis, CA (US); Jason Otto, Plantation, FL (US); Jason Wojcik, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 1425 days.

(21) Appl. No.: 12/333,119

(22) Filed: Dec. 11, 2008

(65) Prior Publication Data

US 2010/0153076 A1 Jun. 17, 2010

(51) Int. Cl.
| G06G 7/60 | (2006.01) |
| G06F 17/10 | (2006.01) |
| A61B 19/00 | (2006.01) |
| G06T 7/00 | (2006.01) |
| G06T 17/20 | (2006.01) |
| A61C 13/00 | (2006.01) |
| G06F 19/00 | (2011.01) |

(52) U.S. Cl.
CPC ............ *A61B 19/50* (2013.01); *G06F 19/3437* (2013.01); *G06T 7/0028* (2013.01); *G06T 17/20* (2013.01); *A61B 19/2203* (2013.01); *A61B 2019/502* (2013.01); *A61B 2019/505* (2013.01); *A61B 2019/5255* (2013.01); *A61C 13/0004* (2013.01); *G06F 19/321* (2013.01); *G06F 19/3481* (2013.01); *G06T 2207/10081* (2013.01); *G06T 2207/30008* (2013.01)

(58) Field of Classification Search
CPC ... A61B 19/50; G06F 19/3437; G06T 7/0028; G06T 17/20

USPC ................................................ 703/11; 600/595
See application file for complete search history.

(56) References Cited

U.S. PATENT DOCUMENTS

| 4,823,807 A | * | 4/1989 | Russell ................. A61B 5/1121 600/586 |
| 5,154,178 A | * | 10/1992 | Shah ................. G01R 33/56391 324/318 |

(Continued)

OTHER PUBLICATIONS

International Search Report and Written Opinion for International Application No. PCT/US2008/086461, Date of Mailing Sep. 4, 2009 (11 pages).

(Continued)

*Primary Examiner* — Michael C Stout
(74) *Attorney, Agent, or Firm* — Foley & Lardner LLP

(57) ABSTRACT

Described are computer-based methods and apparatuses, including computer program products, for implant planning using areas representing cartilage. A predetermined number of control points for generating a predetermined number of areas representing cartilage are determined, wherein the predetermined number of control points are based on an implant component. Measurements corresponding to a plurality of measured cartilage points are received, wherein each cartilage point is based on an associated control point from the predetermined number of control points. A plurality of areas representing cartilage are generated, wherein each area representing cartilage is larger than and projects to an associated control point from the plurality of control points. A representation of the implant component is positioned based on a representation of a bone, the representation of the bone comprising representations of the plurality of areas representing cartilage.

21 Claims, 16 Drawing Sheets

(56) References Cited

U.S. PATENT DOCUMENTS

| | | | | |
|---|---|---|---|---|
| 5,474,088 A * | 12/1995 | Zaharkin | A61B 5/103 128/897 |
| 5,824,085 A * | 10/1998 | Sahay | A61F 2/46 128/898 |
| 5,871,018 A | 2/1999 | Delp et al. | |
| 5,899,859 A * | 5/1999 | Votruba | A61B 5/055 5/601 |
| 6,205,411 B1 * | 3/2001 | DiGioia, III | A61B 17/15 623/901 |
| 6,361,507 B1 * | 3/2002 | Foxlin | 600/595 |
| 6,361,508 B1 * | 3/2002 | Johnson | A61B 5/1123 600/595 |
| 6,533,737 B1 | 3/2003 | Brosseau et al. | 600/595 |
| 6,585,666 B2 * | 7/2003 | Suh | A61B 5/103 600/443 |
| 6,725,173 B2 * | 4/2004 | An | G01V 11/00 244/3.2 |
| 6,786,877 B2 * | 9/2004 | Foxlin | 600/587 |
| 6,820,025 B2 * | 11/2004 | Bachmann | A61B 5/1114 600/595 |
| 6,997,882 B1 * | 2/2006 | Parker | A61B 5/08 600/301 |
| 7,089,148 B1 * | 8/2006 | Bachmann et al. | 702/151 |
| 7,104,998 B2 * | 9/2006 | Yoon | A61B 17/164 600/79 |
| 7,215,124 B1 * | 5/2007 | Purdy | G01R 33/4818 324/309 |
| 7,219,033 B2 * | 5/2007 | Kolen | A63B 60/42 702/150 |
| 7,239,908 B1 | 7/2007 | Alexander et al. | 600/427 |
| 7,387,644 B2 | 6/2008 | Beynnon et al. | 623/20.15 |
| RE43,282 E * | 3/2012 | Alexander et al. | 600/427 |
| 8,421,854 B2 * | 4/2013 | Zerkin | A61B 5/1121 348/77 |
| 2003/0176783 A1 * | 9/2003 | Hu | A61B 5/103 600/429 |
| 2003/0184297 A1 * | 10/2003 | Jakab | G01R 33/285 324/318 |
| 2003/0216661 A1 * | 11/2003 | Davies | A61B 5/04002 600/547 |
| 2004/0006393 A1 * | 1/2004 | Burkinshaw | A61F 2/38 623/20.3 |
| 2004/0019382 A1 * | 1/2004 | Amirouche | A61B 5/0031 623/18.11 |
| 2004/0034313 A1 * | 2/2004 | Leitner | A61B 5/1114 600/595 |
| 2004/0087869 A1 | 5/2004 | Treppo et al. | 600/547 |
| 2004/0091140 A1 * | 5/2004 | Arakawa | G06T 7/60 382/132 |
| 2004/0153079 A1 * | 8/2004 | Tsougarakis et al. | 606/77 |
| 2005/0054917 A1 * | 3/2005 | Kitson | A61B 90/36 600/427 |
| 2005/0197814 A1 * | 9/2005 | Aram | A61F 2/30942 703/11 |
| 2005/0251026 A1 * | 11/2005 | Stone | A61B 17/175 600/424 |
| 2005/0251065 A1 * | 11/2005 | Henning | A61B 5/1076 600/587 |
| 2006/0004284 A1 * | 1/2006 | Grunschlager | A61B 6/00 600/416 |
| 2006/0015030 A1 | 1/2006 | Poulin et al. | |
| 2006/0015120 A1 * | 1/2006 | Richard | 606/102 |
| 2006/0020177 A1 * | 1/2006 | Seo | A61B 5/222 600/300 |
| 2006/0089657 A1 * | 4/2006 | Broers | A61B 5/103 600/102 |
| 2006/0122541 A1 * | 6/2006 | Tuma | A61B 5/107 600/587 |
| 2006/0142657 A1 * | 6/2006 | Quaid | A61B 17/1764 600/424 |
| 2006/0257379 A1 * | 11/2006 | Giordano | A61B 5/1076 424/93.7 |
| 2006/0270949 A1 * | 11/2006 | Mathie | A61B 5/0002 600/595 |
| 2006/0282023 A1 * | 12/2006 | Leitner | A61B 5/103 600/595 |
| 2007/0015995 A1 | 1/2007 | Lang et al. | 600/407 |
| 2007/0032748 A1 * | 2/2007 | McNeil | A61B 5/1038 600/595 |
| 2007/0043287 A1 * | 2/2007 | Degraaf | A61B 5/055 600/410 |
| 2007/0179626 A1 * | 8/2007 | de la Barrera | A61B 17/025 623/20.14 |
| 2007/0219561 A1 * | 9/2007 | Lavallee | A61B 17/025 606/90 |
| 2007/0219639 A1 | 9/2007 | Otto et al. | |
| 2007/0226986 A1 * | 10/2007 | Park | A61B 17/155 29/592 |
| 2007/0249967 A1 * | 10/2007 | Buly | A61B 5/1121 600/595 |
| 2008/0058945 A1 * | 3/2008 | Hajaj | A61F 2/38 623/20.14 |
| 2008/0162074 A1 * | 7/2008 | Schneider | A61B 90/36 702/150 |
| 2008/0177203 A1 | 7/2008 | von Jako | 600/587 |
| 2008/0195109 A1 * | 8/2008 | Hunter | A61B 17/155 606/87 |
| 2008/0202200 A1 * | 8/2008 | West | A61B 6/12 73/1.79 |
| 2008/0211768 A1 * | 9/2008 | Breen | G06F 3/012 345/157 |
| 2008/0243127 A1 * | 10/2008 | Lang | A61B 5/4528 606/87 |
| 2008/0262812 A1 * | 10/2008 | Arata | A61B 19/50 703/11 |
| 2008/0285805 A1 * | 11/2008 | Luinge | G06F 3/011 382/107 |
| 2009/0000627 A1 * | 1/2009 | Quaid et al. | 128/898 |
| 2009/0012532 A1 * | 1/2009 | Quaid et al. | 606/130 |
| 2009/0040224 A1 * | 2/2009 | Igarashi | G06T 19/00 345/427 |
| 2009/0164024 A1 * | 6/2009 | Rudan | A61F 2/4657 623/22.15 |
| 2009/0209884 A1 * | 8/2009 | Van Vorhis | 600/595 |
| 2009/0248044 A1 * | 10/2009 | Amiot | A61B 19/5244 606/130 |
| 2009/0270868 A1 * | 10/2009 | Park | A61B 17/15 606/87 |
| 2009/0292227 A1 * | 11/2009 | Scholten | A61B 5/1117 600/595 |
| 2009/0312973 A1 * | 12/2009 | Hatlestad | A61B 5/103 702/85 |
| 2009/0324078 A1 * | 12/2009 | Wu | G06T 7/0083 382/173 |
| 2010/0063508 A1 * | 3/2010 | Borja | A61B 17/154 606/88 |
| 2010/0063509 A1 * | 3/2010 | Borja et al. | 606/88 |
| 2010/0064216 A1 * | 3/2010 | Borja et al. | 715/705 |
| 2010/0069911 A1 * | 3/2010 | Borja et al. | 606/88 |
| 2010/0113980 A1 * | 5/2010 | Herr | A61F 2/60 600/587 |
| 2010/0137869 A1 * | 6/2010 | Borja et al. | 606/88 |
| 2010/0153081 A1 * | 6/2010 | Bellettre | G06F 19/3437 703/11 |
| 2010/0192662 A1 * | 8/2010 | Yanni | G01P 21/00 73/1.38 |
| 2010/0198067 A1 * | 8/2010 | Mahfouz | A61B 5/1036 600/443 |
| 2010/0211077 A1 * | 8/2010 | Couture | A61B 17/154 606/88 |
| 2010/0234770 A1 * | 9/2010 | Colombet | A61B 5/064 600/595 |
| 2010/0256504 A1 * | 10/2010 | Moreau-Gaudry | A61B 5/0066 600/476 |
| 2010/0298661 A1 * | 11/2010 | McCombie | A61B 5/02028 600/301 |
| 2010/0324457 A1 * | 12/2010 | Bean | A61B 5/4519 600/595 |
| 2011/0028865 A1 * | 2/2011 | Luinge | A61B 5/1038 600/595 |
| 2011/0029116 A1 * | 2/2011 | Jordan | A61B 17/155 700/98 |

(56) References Cited

U.S. PATENT DOCUMENTS

| | | | |
|---|---|---|---|
| 2011/0213275 A1* | 9/2011 | Boos | A61B 5/1071 600/595 |
| 2012/0093377 A1* | 4/2012 | Tsougarakis et al. | 382/128 |
| 2012/0172712 A1* | 7/2012 | Bar-Tal | 600/424 |
| 2012/0203140 A1* | 8/2012 | Malchau | A61B 5/1114 600/595 |

OTHER PUBLICATIONS

International Search Report and Written Opinion for International Application No. PCT/US2008/086462, Date of Mailing Aug. 27, 2009 (14 pages).

Office Action from European Application No. 08 876 503.7, dated Apr. 28, 2014, 3 pages.

* cited by examiner

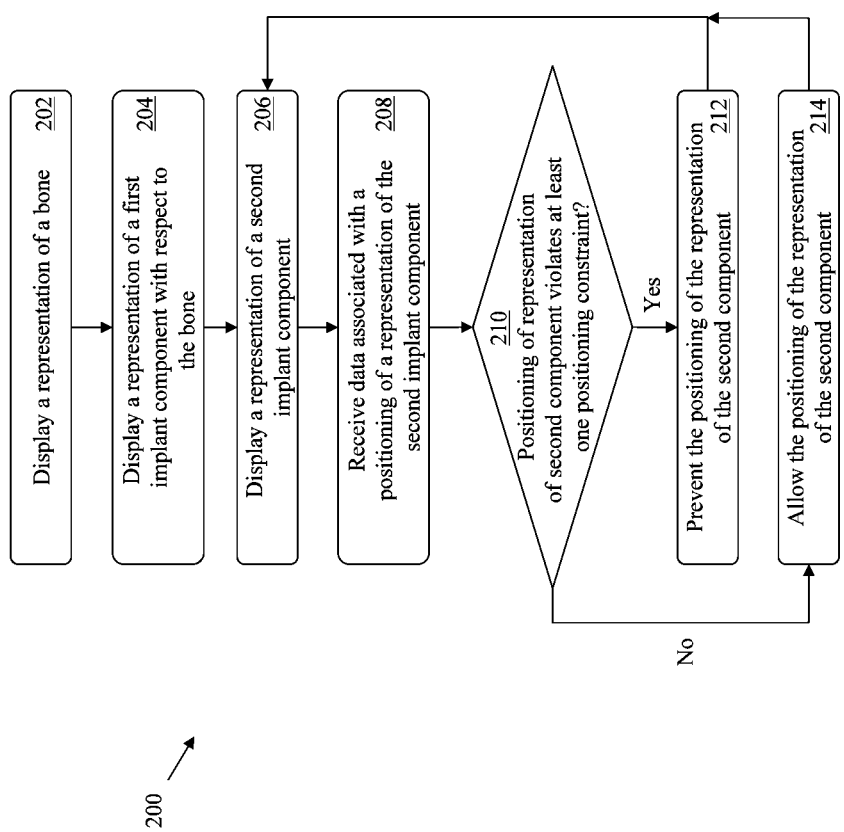

IMPLANT PLANNING USING AREAS REPRESENTING CARTILAGE

CROSS REFERENCES TO RELATED APPLICATIONS

This application relates to and is assigned to the same entity as the co-pending application, entitled "Implant Planning for Multiple Implant Components Using Constraints" U.S. patent application Ser. No. 12/333,109, filed on Dec. 11, 2008, the disclosure of which is hereby incorporated herein by reference in its entirety.

FIELD OF THE INVENTION

The present invention relates generally to surgical computer systems, including computer program products, and methods for implant planning using areas representing cartilage, particularly to estimating areas representing cartilage.

BACKGROUND

Orthopedic joint replacement surgery may involve arthroplasty of a knee, hip, or other joint (e.g., shoulder, elbow, wrist, ankle, fingers, etc.). For example, traditional total knee arthroplasty (TKA) involves a long incision, typically in a range of about 6 to 12 inches, to expose the joint for bone preparation and implantation of implant components. The invasive nature of the incision results in a lengthy recovery time for the patient. Minimally invasive surgery (MIS) reduces the incision length for a total knee replacement surgery to a range of about 4 to 6 inches. However, the smaller incision size reduces a surgeon's ability to view and access the anatomy of a joint. Consequently, the complexity of assessing proper implant position and reshaping bone increases, and accurate placement of implants may be more difficult. Inaccurate positioning of implants compromises joint performance. For example, one problem with TKA is that one or more components of the implant may improperly contact the patella, which may be caused by inaccurate positioning of the one or more implant components within the knee.

An important aspect of implant planning concerns variations in individual anatomies. As a result of anatomical variation, there is no single implant design or orientation of implant components that provides an optimal solution for all patients. Conventional TKA systems typically include a femoral component that is implanted on the distal end of the femur, a tibial component that is implanted on the proximal end of the tibia, and a patellar component that replaces the articular surface of the patella. As mentioned above, conventional TKA systems require an incision large enough to accept implantation of the femoral and tibial components. Further, the femoral and tibial components have standard, fixed geometries and are only available in a limited range of sizes. As a result, the surgeon may be unable to achieve a fit that addresses each patient's unique anatomy, ligament stability, and kinematics.

Modular TKA knee prostheses comprising multiple components that are inserted separately and assembled within the surgical site have been developed to overcome conventional TKA systems. Some modular TKA system implementations mimic a conventional TKA system by allowing the multiple components to be inserted separately so the components can be connected together inside the patient's body. One disadvantage is that the modular components, once assembled inside the patient's body, mimic a conventional TKA system and thus suffer from similar limitations. Once the modular components are fixed together, the components are dependent upon one another. Such implant systems do not enable the surgeon to vary the placement or geometry of each modular component to best suit each patient's unique anatomy, ligament stability, kinematics, and disease state.

Some modular TKA system implementations allow the implant components to be positioned independently of one another. An example of independent component placement systems and methods is described in U.S. patent application Ser. No. 11/684,514, filed Mar. 9, 2007, published as Pub. No. 2008/0058945, and hereby incorporated by reference herein in its entirety. One disadvantage of such systems is the determination of the placement of each implant component is not constrained based on the other implant components. Multiple component implant systems, however, often require that a number of relative constraints between the components be satisfied so that the implant system functions properly. If all implants are planned independently, it is nearly impossible to satisfy all the necessary constraints. For example, in order to have a smooth transition between the femoral condyle implant and the patella implant, the relative position of the two implants to each other is critical.

Further, proper placement of the implant components on the femur and tibia require knowledge of the articular cartilage surfaces of each bone. Articular cartilage is an avascular soft tissue that covers the articulating bony ends of joints. During joint motion, cartilage acts as a lubricating mechanism in the articulating joints and protects the underlying bony structure by minimizing peak contact force at the joint. A model of each bone can be generated from a CT scan of the bone to allow models of the implant components to be positioned relative to the bone models to plan for the surgery. However, CT scans may not accurately determine the articular cartilage surface of the bone. As a result, the planned placement of the implant components match only the surface of the bone and not the cartilage, while the surface of the cartilage frequently determines the optimal placement of the implant. Cartilage surfaces can be determined by capturing the tip positions of a tracked probe while the probe is dragged over the cartilage surface. However, this requires that each point is captured to draw the cartilage surface, which is a timely and computationally involved procedure.

In view of the foregoing, a need exists for surgical methods and devices which can overcome the aforementioned problems so as to enable intraoperative implant planning for accurate placement and implantation of multiple joint implant components providing improved joint performance; consistent, predictable operative results regardless of surgical skill level; sparing healthy bone in minimally invasive surgery; achieving a fit of the implant components that address each patient's unique anatomy, ligament stability, and kinematics; and reducing the need for replacement and revision surgery.

SUMMARY OF THE INVENTION

The techniques described herein provide methods, apparatuses, and computer program products for implant planning for multiple implant components using constraints and implant planning using areas representing cartilage. Such implant planning facilitates the accurate placement of implant components of a multiple component implant to fit the unique anatomy of a patient.

In one aspect there is a method. The method is a surgical planning computerized method for displaying a representation of a bone and a representation of a first implant component with respect to the representation of the bone. The method also includes displaying a representation of a second implant component, wherein the first implant component and the second implant component are physically separated and not connected to each other. The method also includes preventing a positioning of the representation of the second implant component that violates at least one positioning constraint, wherein the positioning constraint is based on the representation of the first implant component.

In another aspect, there is a method. The method is a surgical planning computerized method for displaying a representation of a bone and a representation of a first implant component with respect to the representation of the bone. The method also includes receiving data associated with a positioning of a representation of a second implant component, wherein the first implant component and the second implant component are physically separated and not connected to each other. The method also includes comparing the data associated with the positioning of the representation of the second implant component with a positioning constraint that is based on the representation of the bone, the representation of the first implant component, or both. The method also includes displaying the representation of the second implant component in accord with the data associated with the positioning of the representation of the second implant component if the data meets the positioning constraint.

In another aspect, there is a system. The system is a surgical planning system including a computer configured to generate a display of a representation of a bone and a representation of a first implant component with respect to the representation of the bone. The computer is also configured to generate a display of a representation of a second implant component, wherein the first implant component and the second implant component are physically separated and not connected to each other. The computer is also configured to prevent a positioning of the representation of the second implant component that violates at least one positioning constraint, wherein the positioning constraint is based on the representation of the first implant component.

In another aspect, there is a computer program product. The computer program product is tangibly embodied in a computer readable medium. The computer program product includes instructions being operable to cause a data processing apparatus to display a representation of a bone and a representation of a first implant component with respect to the representation of the bone. The instructions are also operable to cause a data processing apparatus to display a representation of a second implant component, wherein the first implant component and the second implant component are physically separated and not connected to each other. The instructions are also operable to cause a data processing apparatus to prevent a positioning of the representation of the second implant component that violates at least one positioning constraint, wherein the positioning constraint is based on the representation of the first implant component.

In another aspect, there is a system. The system includes displaying a representation of a bone and a representation of a first implant component with respect to the representation of the bone. The system also includes displaying a representation of a second implant component, wherein the first implant component and the second implant component are physically separated and not connected to each other. The system also includes means for preventing a positioning of the representation of the second implant component that violates at least one positioning constraint, wherein the positioning constraint is based on the representation of the first implant component.

In another aspect, there is a method. The method is a surgical planning computerized method for determining a predetermined number of control points for generating a predetermined number of areas representing cartilage, wherein the predetermined number of control points are based on an implant component. The method also includes receiving measurements corresponding to a plurality of measured cartilage points, wherein each cartilage point is based on an associated control point from the predetermined number of control points. The method also includes generating a plurality of areas representing cartilage, wherein each area representing cartilage is larger than and projects to an associated control point from the plurality of control points. The method also includes positioning a representation of the implant component based on a representation of a bone, the representation of the bone comprising representations of the plurality of areas representing cartilage.

In another aspect, there is a system. The system is a surgical planning system including a computer configured to determine a predetermined number of control points for generating a predetermined number of areas representing cartilage, wherein the predetermined number of control points are based on an implant component. The computer is further configured to generate a plurality of areas representing cartilage, wherein each area representing cartilage is larger than and projects to an associated control point from a plurality of control points. The computer is further configured to position a representation of the implant component based on a representation of a bone, the representation of the bone comprising the plurality of areas representing cartilage. The system also includes a probe configured to measure the plurality of cartilage points, wherein each cartilage point is based on an associated control point from the predetermined number of control points.

In another aspect, there is a computer program product. The computer program product is tangibly embodied in a computer readable medium. The computer program product includes instructions being operable to cause a data processing apparatus to determine a predetermined number of control points for generating a predetermined number of areas representing cartilage, wherein the predetermined number of control points are based on an implant component. The computer program product also includes instructions being operable to cause a data processing apparatus to receive measurements corresponding to a plurality of measured cartilage points, wherein each cartilage point is based on an associated control point from the predetermined number of control points. The computer program product also includes instructions being operable to cause a data processing apparatus to generate a plurality of areas representing cartilage, wherein each area representing cartilage is larger than and projects to an associated control point from the plurality of control points. The computer program product includes instructions being operable to cause a data processing apparatus to position a representation of the implant component based on a representation of a bone, the representation of the bone comprising representations of the plurality of areas representing cartilage.

In another aspect, there is a system. The system includes means for determining a predetermined number of control points for generating a predetermined number of areas representing cartilage, wherein the predetermined number of control points are based on an implant component. The system also includes means for receiving measurements corresponding to a plurality of measured cartilage points, wherein each cartilage point is based on an associated control point from the predetermined number of control points. The system also includes means for generating a plurality of areas representing cartilage, wherein each area representing cartilage is larger than and projects to an associated control point from the plurality of control points. The system also includes means for positioning a representation of the implant component based on a representation of a bone, the representation of the bone comprising representations of the plurality of areas representing cartilage.

In other examples, any of the aspects above can include one or more of the following features. A plurality of areas representing cartilage can be calculated, and a positioning of the representation of the first implant component that violates a second positioning constraint that is based on the plurality of areas representing cartilage can be prevented. The at least one positioning constraint can include a rigid constraint between the representation of the first implant component and the representation of the second implant component, wherein the rigid constraint prevents a positioning of the representation of the second implant component that is independent of the representation of the first implant component.

In some examples, the at least one positioning constraint comprises one or more axes of movement of the representation of the second implant component based on the representation of the first implant component. An axis from the one or more axes can constrain a critical area between the representation of the first implant component and the representation of the second implant component. An axis from the one or more axes can constrain a distance between the representation of the first implant component and the representation of the second implant component. An axis from the one or more axes can be based on an arc between the representation of the first implant component and the representation of the second implant component.

In other examples, preventing comprises preventing a movement of the representation of the second component that is not a rotation around the one or more axes, a translation along the one or more axes, or any combination thereof. A cross-sectional display can be displayed at a cross-section point along an axis from the one or more axes, wherein the cross-sectional display comprises the representation of the first implant component, the representation of the second implant component, the representation of the bone, or any combination thereof. The cross-sectional display can be updated based on a new cross-section point along the axis.

In some examples, the at least one positioning constraint is based on a representation of an extension of an articular surface of at least one of the first implant component and the second implant component. An overlap of the representation of the extension of the articular surface and the representation of the first implant component, the representation of the second implant component, or any combination thereof can be determined. The representation of the extension of the articular surface can be displayed. Displaying the representation of the second implant component can include displaying the representation of the second implant component with respect to the representation of the bone.

In other examples, displaying the representation of the second implant component with respect to the representation of the bone further comprises displaying the representation of the second implant component based on at least one of a coordinate space of the representation of the bone or a coordinate space of the representation of the first implant component. A change indicator can be displayed, wherein the change indicator is based on a current location of the representation of the first implant component and at least one of an original location of the representation of the first implant component, a coordinate space of the representation of the bone, a coordinate space of the representation of the first implant component, or a coordinate space of a representation of cartilage. Data associated with a positioning of the representation of the second implant component can be received.

In some examples, the computer is further configured to generate a user interface that enables a positioning of either the representation of the first implant component, the representation of the second implant component, or any combination thereof. The computer can be further configured to calculate a plurality of areas representing cartilage and to adjust a positioning of at least one of the representation of the first implant component and the representation of the second implant component based on at least one of the plurality of areas representing cartilage. The representation of the implant component can be automatically aligned to fit the plurality of areas representing cartilage.

In other examples, generating the plurality of areas representing cartilage includes transforming the predetermined number of control points to a coordinate space of the representation of the bone and transforming the plurality of cartilage points to the coordinate space of the representation of the bone. Generating the plurality of areas representing cartilage can include, for each area representing cartilage from the plurality of areas, calculating a distance between a point of the representation of the bone and an associated transformed cartilage point, calculating a direction between a closest point of the representation of the bone to an associated transformed control point, determining a plurality of points of the representation of the bone that are within a second distance from the associated transformed control point, and adjusting the plurality of points based on the second distance and direction to form the plurality of areas representing cartilage.

In some examples, each of the plurality of points of the representation of the bone corresponds to a set of polygons from a superset of polygons, the representation of the bone comprising the superset of polygons. Adjusting can include adjusting a vertex of each polygon from the set of polygons. The superset of polygons can include triangles. Calculating the distance between the point of the representation of the bone and the associated transformed cartilage point can include selecting a closest point of the representation of the bone to the associated transformed cartilage point.

In other examples, for each area representing cartilage of the plurality of areas representing cartilage, registering a control point from the transformed predetermined number of control points to a closest point in the area representing cartilage. The registered control point can be constrained to automatically adjust a position of the representation of the implant component. The representation of the bone can be displayed, and the representation of the implant component with respect to the representation of the bone can be displayed. A representation of a second implant component can be displayed, wherein the implant component and the second implant component are components of a multiple component implant. The method can include determining if a positioning of the representation of the second implant component violates at least one positioning constraint.

In some examples, the at least one positioning constraint is based on the representation of the bone, the representation of the implant component, or any combination thereof. The computer can be further configured to generate a display of a second implant component, wherein the implant component and second implant component are components of a multiple component implant. The computer can be further configured to determine if a positioning of the representation of the second implant component violates at least one positioning constraint. The at least one positioning constraint can be based on the representation of the bone, the representation of the implant component, or both. The computer can be further configured to generate a user interface that enables a positioning of either the representation of the implant component, the representation of the second implant component, or any combination thereof.

The techniques for implant planning for multiple implant components using constraints and implant planning using areas representing cartilage described herein can provide one or more of the following advantages. Since each patient's anatomy is unique, having multiple sizes and shapes for the implant components and constraining the positioning of the components with respect to other components and/or the bone allows the system to find a best fit for each patient. The constraints provide information on positioning the components accurately and effectively, preventing improper placement, and enabling the multiple components of the implant to work with each other as they were designed to do so. Multiple types of visual displays further enhance proper placement of the implant components. Further, implant components can be adjusted to account for cartilage representations. A more effective, less intrusive implant planning procedure can be achieved for each individual patient. Implant planning using constraints allows the placement of components that are physically separated and not touching to be optimally placed within a patient's anatomy at locations which ensure the components operate as designed. Optimal positioning of smaller, separate components allows for smaller incisions (e.g., due to the smaller components) and less invasive surgeries.

Other aspects and advantages of the present invention will become apparent from the following detailed description, taken in conjunction with the accompanying drawings, illustrating the principles of the invention by way of example only.

BRIEF DESCRIPTION OF THE DRAWINGS

The foregoing and other objects, features, and advantages of the present invention, as well as the invention itself, will be more fully understood from the following description of various embodiments, when read together with the accompanying drawings.

FIG. 3 illustrates an exemplary method for implant planning with constraints for components of a multiple component implant;

FIGS. 10A-10C illustrate implant points on implant components of a multiple component implant for implant planning;

DETAILED DESCRIPTION

Figure 1:
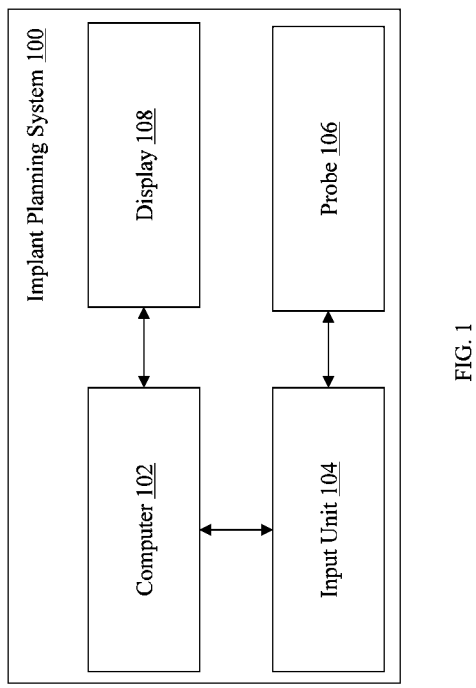
FIG. 1 illustrates an exemplary multiple component implant planning system according to the present invention.

Presently preferred embodiments are illustrated in the drawings. Although this specification refers primarily to knee joint replacement surgery, it should be understood that the subject matter described herein is applicable to other joints in the body, such as, for example, a shoulder, elbow, wrist, spine, hip, or ankle and to any other orthopedic and/or musculoskeletal implant, including implants of conventional materials and more exotic implants, such as orthobiologics, drug delivery implants, and cell delivery implants.

In general overview, multiple component implant planning is achieved by constraining the adjustment of the individual components of the multiple component implant. Each component can be adjusted based on the constraints, allowing a proper fit for each implant component while preventing improper placement. FIG. 1 illustrates an exemplary multiple component implant planning system 100 according to the present invention. The system includes computer 102. Computer 102 is in communication with input unit 104. Input unit 104 is in communication with probe 106. Computer 102 is further in communication with display 108.

The computer 102 may be any known computing system but is preferably a programmable, processor-based system. For example, the computer 102 may include a microprocessor, a hard drive, random access memory (RAM), read only memory (ROM), input/output (I/O) circuitry, and any other well-known computer component. The computer 102 is preferably adapted for use with various types of storage devices (persistent and removable), such as, for example, a portable drive, magnetic storage (e.g., a floppy disk), solid state storage (e.g., a flash memory card), optical storage (e.g., a compact disc or CD), and/or network/Internet storage. The computer 102 may comprise one or more computers, including, for example, a personal computer (e.g., an IBM-PC compatible computer) or a workstation (e.g., a SUN or Silicon Graphics workstation) operating under a Windows, MS-DOS, UNIX, or other suitable operating system and preferably includes a graphical user interface (GUI).

The input unit 104 enables information to be communicated to the implant planning system 100. For example, the input unit 104 provides an interface for a user to communicate with the implant planning system. The terms user and operator both refer to a person using the implant planning system 100 and are sometimes used interchangeably. The input unit 104 is connected to the computer 102 and may include any device enabling a user to provide input to a computer. For example, the input unit 104 can include a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick. The input unit 104 may also include surgical navigation equipment that provides data to the computer 102. For example, the input unit 104 can include a tracking system for tracking the position of surgical tools and patient anatomy. The tracking system may be, for example, an optical, electromagnetic, radio, acoustic, mechanical, or fiber optic tracking system.

The probe 106 may be any probe for measuring the thickness of articular cartilage. An example of a probe is U.S. Pat. No. 6,585,666 ("the '666 patent"), filed Jul. 30, 2001, and incorporated by reference herein in its entirety. The '666 patent discloses a diagnostic probe which determines the thickness of articular cartilage as a function of the true ultrasound speed of the cartilage. The probe 106 may also be a tracked probe, where tip positions of the probe are captured (e.g., by an optical camera, joint encoders, etc.) when the probe tip is touched to the cartilage surface. Because the patient's bones are in registration with bone models (created, for example, from CT scans of the bones), the captured tip positions can be compared to the known location of the bone surface to estimate the thickness of the cartilage. The tracked probe may be, for example, a probe having optical markers affixed thereto or an end effector of an articulated or robotic arm.

The probe 106 is in operative communication with the computer 102. For example, the probe 106 may be coupled to the computer 102 via an interface (not shown). The interface can include a physical interface and/or a software interface. The physical interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system). The software interface may be resident on the computer 102. For example, in the case of a tracked probe that includes optical markers, probe tip position data is captured and relayed to the computer 102 by an optical camera.

The display 108 is a visual interface between the computer 102 and the user. The display 108 is connected to the computer 102 and may be any device suitable for displaying text, images, graphics, and/or other visual output. For example, the display 108 may include a standard display screen (e.g., LCD, CRT, plasma, etc.), a touch screen, a wearable display (e.g., eyewear such as glasses or goggles), a projection display, a head-mounted display, a holographic display, and/or any other visual output device. The display 108 may be disposed on or near the computer 102 (e.g., mounted within a cabinet also comprising the computer 102) or may be remote from the computer 102 (e.g., mounted on a wall of an operating room or other location suitable for viewing by the user). The display 108 is preferably adjustable so that the user can position/reposition the display 108 as needed during a surgical procedure. For example, the display 108 may be disposed on an adjustable arm (not shown) or on any other location well-suited for ease of viewing by the user. The display 108 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), digital or video images, registration information, calibration information, patient data, user data, measurement data, software menus, selection buttons, status information, and the like. The terms model and representation can be used interchangeably to refer to any computerized display of a component (e.g., implant, bone, tissue, etc.) of interest.

Figure 2:
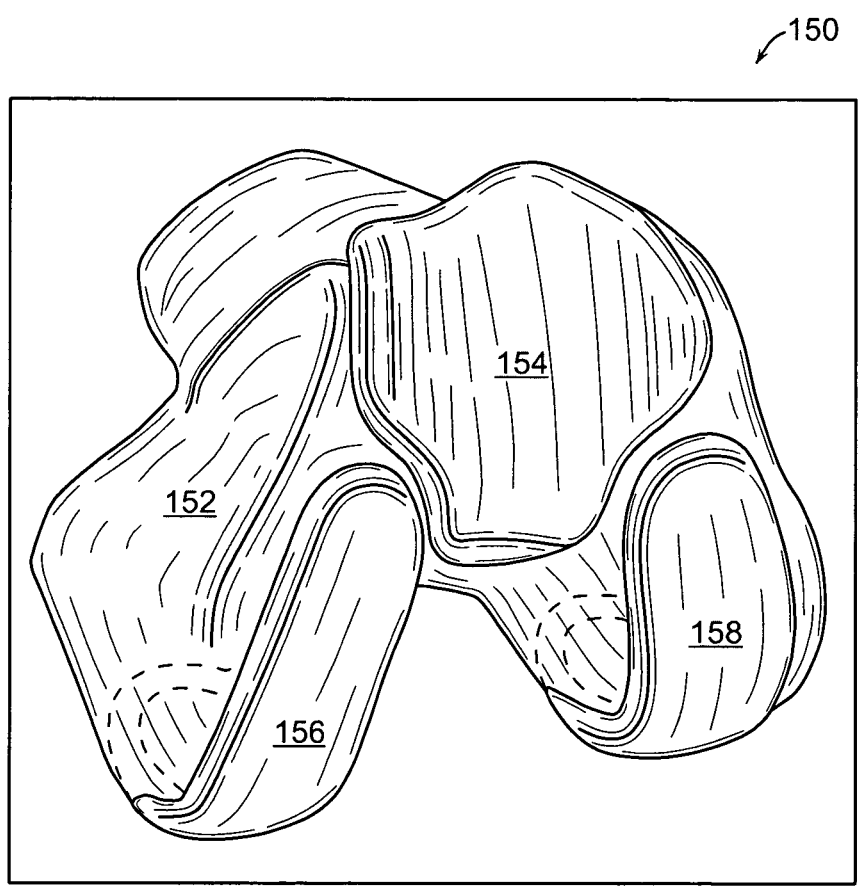
FIG. 2 is a perspective view of a femur and representations of components of an exemplary multiple component implant as presented by the display of FIG. 1.

In some embodiments, the display 108 displays graphical representations of the bones associated with a joint of interest (e.g., the femur and tibia of a knee joint). The display 108 can further display graphical representations of one or more components of a multiple component implant. FIG. 2 is a perspective view 150 of a representation of a femur 152 and representations of components of an exemplary multiple component implant as presented by the display 108 of FIG. 1. The representation of the multiple component implant includes a central patello-femoral implant component 154 and a medial implant component 156. The representation of the multiple component implant may further include a lateral implant component 158. The display 108 can allow a user to position one or more of the implant component representations (e.g., the patello-femoral implant component 154, the medial implant component 156, and/or the lateral implant component 158). The positioning of the representations of the implant components can be based on constraints, as will be discussed further below. The representations of components and/or bones can be semi-transparent to demonstrate the relationship among the components and/or bones. For example, in FIG. 2, the representation of the femur 152 is semi-transparent so the portions of both the medial implant component 156 and the lateral implant component 158 located under the representation of the femur 152, which would normally be hidden, can be viewed by a user of the implant planning system 100.

The components of the multiple component implant are preferably segmented components. As shown in FIG. 2, a segmented component is an individual component implanted on the bone as an independent, self-contained, stand-alone component that is not physically constrained by any other component of the multiple component implant (as used herein, the term physically constrained means that the components are linked through a physical connection and/or physical contact in such a manner that the link between the components imposes limitations on the positioning or placement of either of the components). Thus, the representation of the patello-femoral implant component 154, the representation of the medial implant component 156, and the representation of the lateral implant component 158 are all segmented components. To ensure that a segmented component is not physically constrained by other components, the segmented component may be implanted in the joint so that the component is not connected to and/or in contact with any other segmented component.

For example, the components of the multiple component implant are configured such that the components can be implanted on a patient's femur without being connected, as shown in FIG. 2. While FIG. 2 shows a graphical representation of both the implant components and the bone, the representations of the implant components and the bone are indicative of the actual implantation of the implant components on a patient's bone as represented by FIG. 2. For example, for perspective view 150, the representation of the patello-femoral implant component 154, the representation of the medial implant component 156, and the representation of the lateral implant component 158 are not interconnected when fixed relative to the representation of the femur 152. Similarly, during the actual implant procedure for the implant components, the patello-femoral implant component, the medial implant component, and the lateral implant component are not interconnected when fixed relative to the patient's femur. Providing perspective view 150 (e.g., through display 108 of the implant planning system 100) advantageously allows a user to plan the implant procedure before a patient surgery to maximize the effectiveness of the implant while minimizing the invasiveness of the surgery to the patient.

For example, the system of three implant components (e.g., components 154, 156, and 158) can be rotated and translated as one rigidly attached system to an initial location in the joint. The initial location can match the representation of the implant to the representation of one or more bones and/or the representation of the cartilage surface on the one or more bones. For example, FIG. 2 shows the representations of the three implant components aligned on the representation of the femur 152. Once the overall location and orientation have been set, individual components (e.g., the medial implant component 156) can be rotated around one or more predefined axes. The axes can be defined, for example, in the coordinate space of a reference component representation, the representation of the bone, or any other displayed representation (e.g., the axes can be defined in the coordinate space of the central patello-femoral implant component 154).

In some embodiments the graphical displays are configured to provide for easy identification of different items within the display. Items can be visually distinguished from other items in the display through visual aids, such as color-coding, hatching, and shading. In some embodiments, all the representations of components of a multiple component implant are displayed with the same visual aid. In some embodiments, the representation of the bone and each implant component representation is displayed with a unique visual aid to facilitate easy identification of the implant component and the bone representations.

The graphical displays are used to provide the user with a simulation of positioning the implant components on a patient's anatomy preoperatively. The bone representation and implant component representations can be generated to the scale of the true component/bone relative sizes and shapes. Advantageously, the implant component representations can be positioned (e.g., by an operator) on the bone representation, and the bone representation can be moved to mimic actual position changes of the bone that would occur post-operatively as the joint moves through a range of motion, as described, for example, in U.S. patent application Ser. No. 11/963,547, filed Dec. 21, 2007, and hereby incorporated by reference herein in its entirety. An operator can then adjust the implant component representations to find an optimal positioning of the implant components along the bone prior to surgery.

FIG. 3 illustrates an exemplary method 200 for implant planning with constraints for components of a multiple component implant, which will be explained with reference to FIG. 2. The system (e.g., the implant planning system 100 of FIG. 1) displays (202) a representation of a bone (e.g., on display 108). For example, the system displays a three-dimensional representation of the femur 152 (i.e., a three-dimensional graphical model of a patient's bone). The displayed bone representation can also be a two-dimensional representation. For example, the bone representation can be a cross-sectional representation of the bone. The graphical model of the bone may be generated in various ways. For example, as described in U.S. patent application Ser. No. 12/147,997, filed Jun. 27, 2008, and hereby incorporated by reference herein in its entirety, multiple sequential images of a patient's anatomy are segmented to discern the outline of the anatomy and propagated to adjacent images to generate a three-dimensional model of the patient's anatomy. Alternatively, for 3D imageless planning, bone atlases may be used to obtain the 3D bone models. A bone atlas is a statistical model that represents the relevant anatomy, including information on natural variations typically existing in specific populations with specific distributions and probabilities. Using known image processing techniques and statistical data, the bone atlas may be transformed or "morphed" to find a best fit to the patient's anatomy based on demographic information, such as gender, age, stage of disease, and other patient-specific characteristics. Additionally, although preoperative planning can be accomplished using the initial bone atlas model, once intra-operative registration data on the actual physical bones is obtained, the bone atlas can be further morphed to improve the fit to the patient's anatomy along with corresponding adjustments to the implant plan. The system displays (204) a representation of at least a first implant component with respect to the bone. For example, the system displays the central patello-femoral implant component 154 with respect to the representation of the femur 152. The system and/or operator can position the implant component representation with respect to a base planning coordinate space. The base planning coordinate space can be, for example, the coordinate space of the representation of the bone. For CT image-based bone models, this corresponds to the coordinate space of the CT scan of the patient's bone. Positioning by the operator can be accomplished using any input means (e.g., input unit 104, a keyboard, mouse, touch screen display, and/or the like).

The representation of an implant component can be a two-dimensional and/or a three-dimensional model. The model can be stored on the implant planning system 100. There can be multiple models for each component to represent implant component systems of various sizes and shapes. Advantageously, since each patient's anatomy is unique, having multiple sizes and shapes for the implant components allows the system to find a best fit for each patient (e.g., based on bone shape and size, joint movement, cartilage depth, and other physical characteristics unique to the patient). For example, depending on the representation of the bone, the system and/or operator can choose a component system from a plurality of component systems that best fits the representation of the bone.

The system 100 displays (206) a representation of a second implant component. For example, the system 100 displays medial implant component 156. The system 100 receives (208) data associated with a positioning of a representation of the second implant component. For example, an operator can use the implant planning system 100 to adjust the multiple component representations during an implant planning procedure to optimize component placement for a patient. The operator can, for example, reposition the medial implant component 156. The operator can reposition the medial implant component 156 using any input means (e.g., input unit 104, a keyboard, mouse, touch screen display, and/or the like). In some embodiments, steps 204 and 206 occur simultaneously. For example, the system displays the representations of the first and second implants, and the system and/or operator can position the implant component representations with respect to the base planning coordinate space. For example, the operator can rotate and/or translate the multiple implant components as one rigidly attached system to an initial location relative to the representation of the bone.

The system 100 determines (210) if the positioning of the representation of the second component violates at least one positioning constraint. Positioning constraints (see, e.g., FIG. 4A) allow an operator to move component representations within certain limits to ensure, for example, the components operate properly, are non-intrusive to the patient's anatomy, and are positioned correctly. Constraints can be associated with points, axes, lines, volumes, and/or other constraints. For example, constraints prevent an operator from positioning a component representation in an improper location. If the system 100 determines the positioning of the representation of the second component violates a positioning constraint, the system 100 prevents (212) the positioning of the second implant component (e.g., the representation of the component on the display will not move as requested by the input of the operator). If the system 100 determines the positioning does not violate the positioning constraint, the system 100 allows (214) the new positioning. The system 100 can update the display to reflect the new positioning of the second implant component. In cases where the system 100 prevents the positioning of the second implant, the system 100 can optionally provide an error message to the operator indicating why the second implant cannot be moved to the desired position.

Figure 4A:
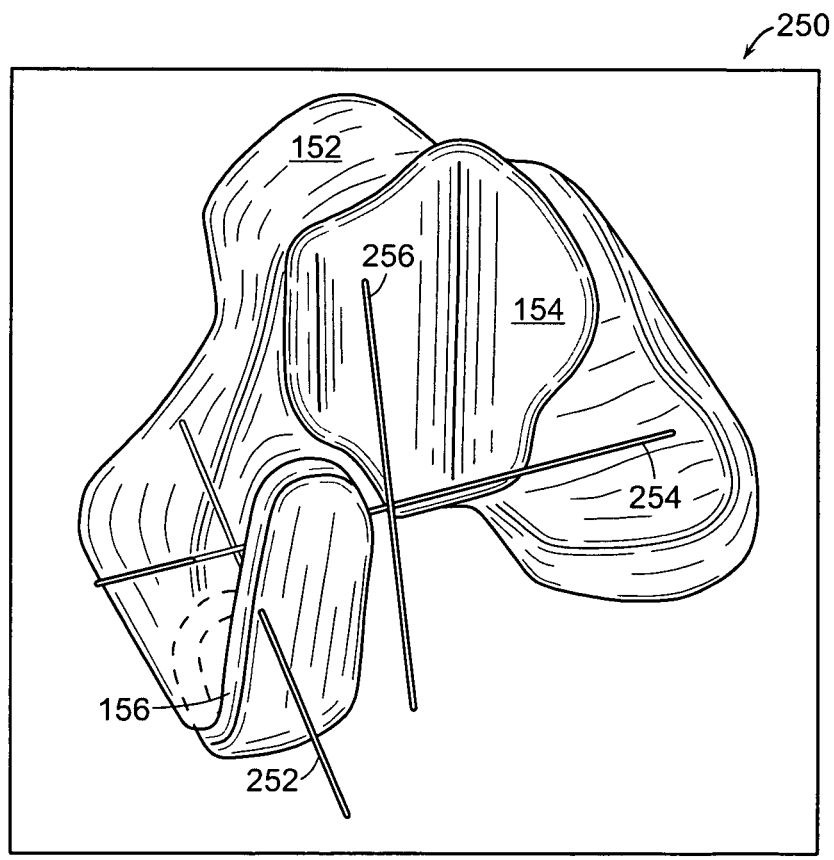
FIG. 4A illustrates a prospective display including constraints for representations of components of a multiple component implant.

FIG. 4A illustrates a display 250 including constraints for representations of components of a multiple component implant. The display 250 includes the representation of the femur 152, the representation of the patello-femoral implant component 154, and the representation of the medial implant component 156. The display 250 includes three constraint axes, axes 252, 254, and 256. The constraints can be visually distinguished from other items in the display through visual aids, such as color-coding, hatching, and shading. While the display 250 includes three constraint axes, the display 250 can include any number of constraint axes. Those skilled in the art can appreciate that the constraints can be applied to any component of the multiple component implant.

The constraint axes shown in FIG. 4A constrain the movement of the medial implant component 156 relative to the axes. The constraint axes can constrain the movement of the implant component based on one or more other implant components, the representation of the bone, or a representation of cartilage (see, e.g., FIGS. 3-7). For example, the constraint axes can constrain the movement of the medial implant component 156 based on the patello-femoral implant component 154 or the representation of the femur 152.

The constraints can be axes of rotation and/or translation directions defined relative to any coordinate space (e.g., anatomic bone or implant). In some embodiments, the constraint axes can be transformed from the implant coordinate space into the base planning coordinate space (e.g., the coordinate space of the representation of the bone). For example, let $C_B$=the base planning coordinate space;
$C_{I1}$=the coordinate space of a first (1) implant (I) component;
$C_{I2}$=the coordinate space of a second (2) implant (I) component;
$T_{I1}$=homogenous (rigid body) transformation matrix for the transformation from the coordinate space of the first (1) implant (I) component to the base planning coordinate space; and
$T_{I2}$=homogenous (rigid body) transformation matrix for the transformation from the coordinate space of the second (2) implant (I) component to the base planning coordinate space.

The rigid body transformation matrices perform translations while preserving Euclidean distances between coordinate locations. Homogeneous coordinate transformation matrices operate on four-dimensional homogenous coordinate vector representations of traditional three-dimensional coordinate locations. Instead of representing each point (x,y,z) in a three-dimensional space with a single three-dimensional vector:

$$\begin{bmatrix} x \\ y \\ z \end{bmatrix} \quad \text{Equation 1}$$

homogenous coordinates allow each point (x,y,z) to be represented by any of an infinite number of four dimensional vectors, which when multiplied by 1.0 results in the vector:

$$\begin{bmatrix} x \\ y \\ z \\ 1.0 \end{bmatrix} \quad \text{Equation 2}$$

The three-dimensional vector corresponding to any four-dimensional vector can be computed by dividing the first three elements by the fourth, and a four-dimensional vector corresponding to any three-dimensional vector can be created by simply adding a fourth element and setting it equal to one. Any three-dimensional linear transformation (e.g., rotation, translation, skew, and scaling) can be represented by a 4×4 homogenous coordinate transformation matrix. For example, a translation can be represented by a 4×4 homogeneous coordinate transformation matrix:

$$\begin{bmatrix} 1 & 0 & 0 & x_s \\ 0 & 1 & 0 & y_s \\ 0 & 0 & 1 & z_s \\ 0 & 0 & 0 & 1 \end{bmatrix} \quad \text{Equation 3}$$

where:
$x_s$=translation along the x-axis;
$y_s$=translation along the y-axis; and
$z_s$=translation along the z-axis.

Multiplying Equation 1 by Equation 2 provides a transformation from a three-dimensional coordinate position (x,y,z) to the three-dimensional coordinate position (x', y', z') as shown below:

$$\begin{bmatrix} x' \\ y' \\ z' \\ 1.0 \end{bmatrix} = \begin{bmatrix} 1 & 0 & 0 & x_s \\ 0 & 1 & 0 & y_s \\ 0 & 0 & 1 & z_s \\ 0 & 0 & 0 & 1 \end{bmatrix} * \begin{bmatrix} x \\ y \\ z \\ 1.0 \end{bmatrix} \quad \text{Equation 4}$$

The first implant component is positioned from $C_{I1}$ to $C_B$ using $T_{I1}$. The second implant component is positioned from $C_{I2}$ to $C_B$ using $T_{I2}$. To transform a point or vector defining a constraint from $C_{I1}$ to $C_{I2}$ so that it can be used to limit the motion of the second implant component during planning, the point or vector is multiplied by the homogeneous matrix, $T_{I1}(T_{I2}^{-1})$, where $T_{I2}^{-1}$ is the inverse of $T_{I2}$. In some examples, the homogeneous matrices can be general transformations from one coordinate space to another.

The representation of the medial implant component 156 can be manipulated based on the constraint axes 252, 254, and 256. For example, the medial implant component 156 can be rotated around the constraint axes, translated along the constraint axes, and/or other movements so that certain constraints (e.g., angles, distances, degrees of rotation, and/or the like) are preserved between the medial implant component 156 and a base object (e.g., the representation of the femur 152 or the representation of the patello-femoral implant component 154). For example, a constraint axis can be defined as an axis which minimizes the effect of the movement of the implant component with respect to a base object (i.e., the representation of the femur 152 or the representation of the patello-femoral implant component 154) for a known area that has a substantial effect on the effectiveness of the overall multiple component implant. By incorporating constraints into the implant system 100, a user of the system 100 can freely position an implant component relative to a patient's bone in a way that does not compromise the effectiveness of the multiple component implant. If the user attempts to position the implant component in a location that could compromise the operation of the implant system, the constraints automatically prevent such positioning of the implant component. As such, the constraints act as an automatic guide for the user, ensuring eventual placement of an implant component that provides for a successful operation of the multiple component implant system.

Any number of constraint axes can be used. A constraint axis can be based on an arc between the representation of a first implant component and a representation of a second implant component. For example, if an implant component comprises an arc-like shape (e.g., the representation of the medial implant component 156 is shaped like an arc to properly fit the rounded surface of the representation of the femur 152), constraints can be based on the arc to preserve a distance between the implant component and other implant components. For example, constraint axis 252 can be based on the arc center of the representation of the medial implant component 156.

A constraint axis can constrain a critical area between two implant components (e.g., an area between the representation of the first implant component patello-femoral implant component 154 and the representation of the medial implant component 156). A critical region can be a region associated with two implant components that can have a large effect on the overall operability of the multiple implant component when one or more components of the multiple component implant are repositioned. For example, constraint axis 254 can be based on an area between the representation of the patello-femoral implant component 154 and the representation of the medial implant component 156 where the two implant components are within a critical distance (e.g., within 3 mm from touching). Axis 254 would constrain movement of the implant components around the critical area to ensure proper positioning.

A constraint axis can constrain a distance between a representation of a first implant component and a representation of a second implant component. For example, constraint axis 256 can be selected as an axis between the representation of the patello-femoral implant component 154 and the representation of the medial implant component 156 so that movement along axis 256 preserves the distance between the representation of the patello-femoral implant component 154 and the representation of the medial implant component 156. The axes can also be constrained based on the representation of the bone (e.g., the representation of the femur 152), a representation of a cartilage area, and/or the like. Translational movements of implant component representations can also be constrained to two dimensions or an arbitrary plane. For example, one constraint is facilitating translation only in the coronal or x/z plane. Another exemplary translational constraint is translation along an arbitrary curve in 3D space. Another exemplary constraint is to anchor the implant component to a specific point. For example, the specific point can be on or off the component, and can be identified in the coordinate system of a second component. For example, the implant can be "tied" to this specific point, but otherwise left unconstrained. Other constraints can include limiting the component to one or more motions within a defined "bounding volume." For example, a two or three-dimensional shape or area can represent the area within which a representation of an implant component can be moved. Movements which attempt to move the implant component outside of the shape or area can be prevented by the system.

Advantageously, displaying the constraint axes provides an operator (e.g., a surgeon) information on positioning the components of a multiple component implant accurately and effectively. For example, constraining the movement of the representation of the medial implant component 156 along the three constraint axes 252, 254, 256 prevents the operator from inadvertently positioning the medial implant component in a location which could be harmful to the patient's patella. Constraints can be used to mirror factors related to the precise, accurate, and functional placement of the components, allowing an operator to safely reposition the location of an implant component without jeopardizing the functionality of the implant. The operator need not know about the factors, rather the factors are built into the system 100 through constraints. The operator is automatically prevented from moving the component in a way which violates the constraints. This advantageously allows the multiple components to be placed according to the patient's anatomy while still optimally working with each other as designed, without the operator having to know such details.

Figure 4B:
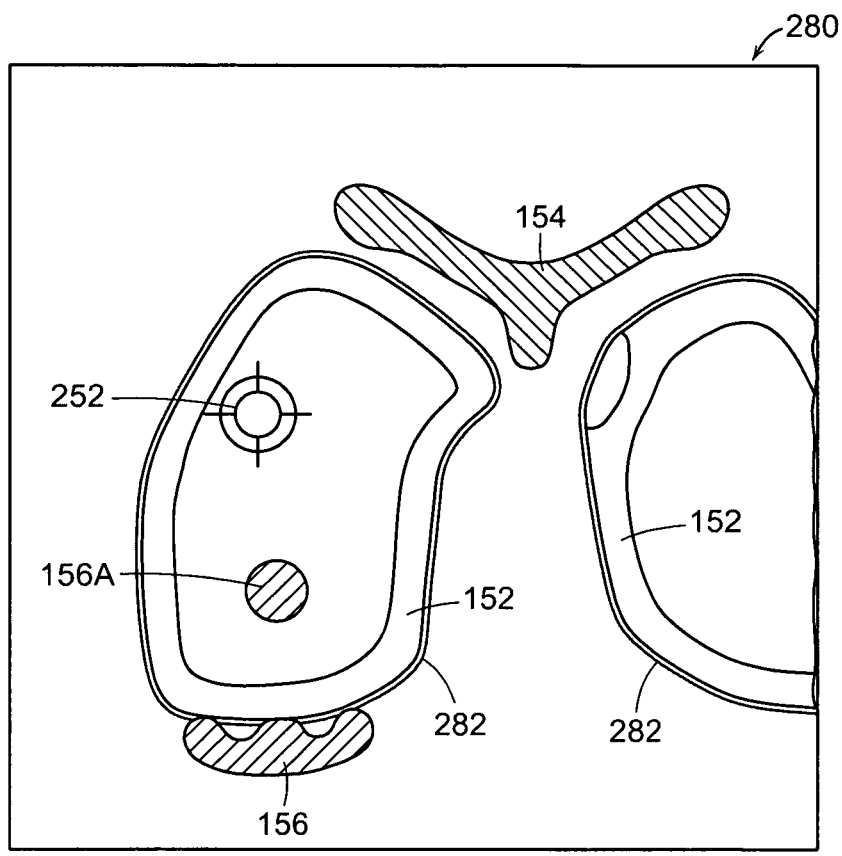
FIG. 4B illustrates a cross-sectional display along a constraint axis including representations of components of a multiple component implant.

FIG. 4B illustrates a cross-sectional display 280 along a constraint axis including representations of components of a multiple component implant. The cross-sectional display 280 is a cross-sectional view of FIG. 4A along constraint axis 252. As such, the cross-sectional display 280 is at a location of the three-dimensional display 250 so that the line representing constraint axis 252 is perpendicular to display 280 (e.g., as if the viewer is looking straight down constraint axis 252 so that constraint axis 252 appears only as a point). Those skilled in the art can appreciate that the cross-sectional display can be generated about any point of the three-dimensional display 250.

The cross-sectional display 280 includes the representation of the femur 152. Because of the location of the cross-sectional display 280 with respect to the three-dimensional display 250, the representation of the bone appears as two separate portions. Subsequent cross-sectional images can be generated along, for example, constraint axis 252 to portray the entire depth of the representation of the bone along constraint axis 252. The cross-sectional display 280 includes the representation of the patello-femoral implant component 154 and the representation of the medial implant component 156. The display 280 includes a portion of the medial implant component 156A located within the representation of the femur 152. This can be, for example, a portion of the representation of the medial implant component 156 which protrudes into the representation of the femur 152 during the operation to affix the medial implant component to the femur (e.g., a post or keel of the medial implant component). The cross-sectional display 280 includes an outline of the segmented bone surface 282. This outline matches the surface which is displayed in the 3D view (e.g., FIG. 4A). The outline of the segmented bone surface 282 can be color-coded to facilitate easy identification (e.g., by a user). For example, the outline of the segmented bone surface can be colored red.

In some embodiments, to constrain the rotation of an implant component around one axis (e.g., the representation of medial implant component 156 about constraint axis 252), the representation of the bone and of the implant can be displayed in the cross-sectional display 280 along the constraint axis. Other movements of the implant component of interest besides movements for the implant component about the constraint axis (e.g., transformations, rotations, and/or the like along other constraint axes) can be disabled for the implant component. The cross-sectional display can be scrolled along the rotation axis, while the center of rotation in the plane is fixed with respect to the constraint axis. With respect to FIG. 4B, the medial implant component 156 can be rotated around constraint axis 252, translated along constraint axis 252, and/or any other movement in relation to constraint axis 252. In some embodiments, another constraint is that the range of each rotation can be limited. For example, the medial implant component 156 can be constrained so it can be rotated around constraint axis 252 within +/−15° from the current location of the medial implant component.

An implant component can be constrained along more than one axis. For example, to constrain the translation of the medial implant component 156 along two axes (e.g., constraint axes 252 and 254), the representations of the bone and the implant component can be displayed in a two-dimensional display in which the plane is defined by the two axes. In some embodiments, the rotations can be disabled. In some embodiments, the translation in each two-dimensional display (e.g., each display based on two axes if multiple axes are present) can be limited to one of the axis.

Figure 5:
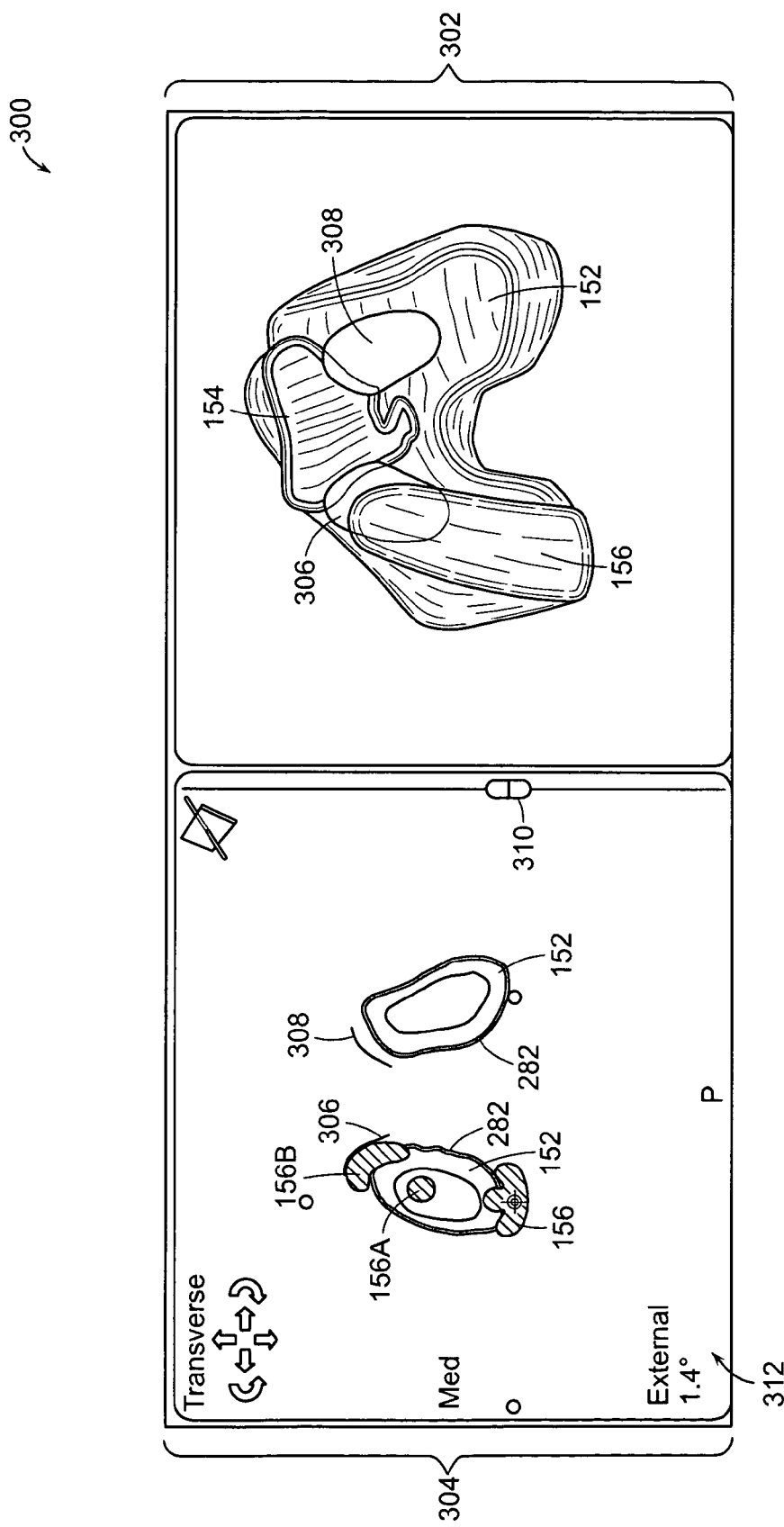
FIG. 5 illustrates a split display including constraints for representations of components of a multiple component implant.

For any step of a surgical planning process, points, models or/and surfaces can be displayed to facilitate the implant component planning. Like constraint axes, these points and surfaces can be defined in an arbitrary space (e.g., the coordinate space of one of the implant components). FIG. 5 illustrates a split display 300 including constraints for representations of components of a multiple component implant. The split display 300 includes a three-dimensional display 302 and a two-dimensional display 304. The display 300 includes an extension surface 306 and an extension surface 308, which are representations of an extension of an articular surface. For example, as shown in FIG. 5, the extension surfaces 306 and 308 may each be a representation of an extension of a portion of the articular surface of the patello-femoral implant component 154. Advantageously, providing both the three-dimensional display 302 and the two-dimensional display 304 with the extension surfaces 306, 308 can provide a user a reference for the ideal placement of the implant component relative to the base object (e.g., the representation of the medial component 156 (implant component) with respect to the representation of the patello-femoral component 154 (base object)). In other examples, the femur 152 can be the base object.

The three-dimensional display 302 includes the representation of the femur 152. The three-dimensional display 302 includes the representation of the patello-femoral implant component 154 and the representation of the medial implant component 156. The three-dimensional display 302 includes the extension surfaces 306, 308. The two-dimensional display 304 includes the representation of the femur 152. The two-dimensional display 304 includes the representation of the patello-femoral implant component 154 and the representation of the medial implant component 156. The two-dimensional display 304 includes extension surfaces 306, 308 and the outline of the segmented bone surface 282. This outline matches the surface which is displayed in the 3D view. The two-dimensional display includes a slider 310 and a change indicator 312. The two-dimensional display 304 is a cross-sectional view of the three-dimensional display. The slider 310 can move the two-dimensional display 304 along an axis which is perpendicular to the three-dimensional display 302 to represent various 2D slices through the three-dimensional display 302. The change indicator 312 can indicate the difference between the coordinate system of a representation of an implant component with reference to a base reference. The base reference can be, for example, an initial position of the representation of the implant component, a base coordinate system (e.g., the coordinate system of the representation of the bone, the coordinate system of the representation of a cartilage area), and any other reference point. The change indicator can represent a degree of change from the base reference, an angle of change from the base reference, a distance from the base reference, and any other metric between the representation of the implant component and the base reference. For example, the change indicator 312 can display a degree of change between the current location of the representation of the implant component and an original representation of the implant component.

The extension surfaces 306, 308 can be, for example, three-dimensional shapes which are drawn between two implant components indicative of the original placement of the two components. For example, the extension surfaces 306, 308 can be the surfaces which would connect the two implant components if the implant components were a single component implant. Movements of the implant components can be constrained by the extension surfaces 306, 308 based on the location of the implant components relative to the extension surfaces 306, 308. As representations of the implant components are adjusted in the implant planning system, the extension surfaces 306, 308 remain fixed based on the original placement location of the implant components prior to adjustment. During adjustment of the implant components, the extension surfaces 306, 308 can be treated as transparent, allowing implant components to "pass through" the extension surfaces 306, 308 if the component is adjusted in a way that protrudes into the shape of the extension surfaces 306, 308. For example, moving the representation of the medial implant component 156 in one direction can cause the representation of the medial implant component 156 to protrude into the representation of extension surface 308. Similarly, moving the representation of the medial implant component 156 can cause a gap to form between the representation of extension surface 308 and the representation of the medial implant component 156. The overlap of the implant components and the extension surfaces 306, 308, the distance between the implant components and the extension surfaces 306, 308, or both can be used to constrain the movement of the implant components relative to the extension surfaces 306, 308. Constraints can include limiting the overlap between a representation of an implant component and one or more corresponding extension surfaces, limiting the distance between a representation of an implant component and one or more corresponding extension surfaces, and constraining other relations between the implant components and the extension surfaces (e.g., constraining rotations, translations, and/or the like between the implant components and the extension surfaces).

Figure 6:
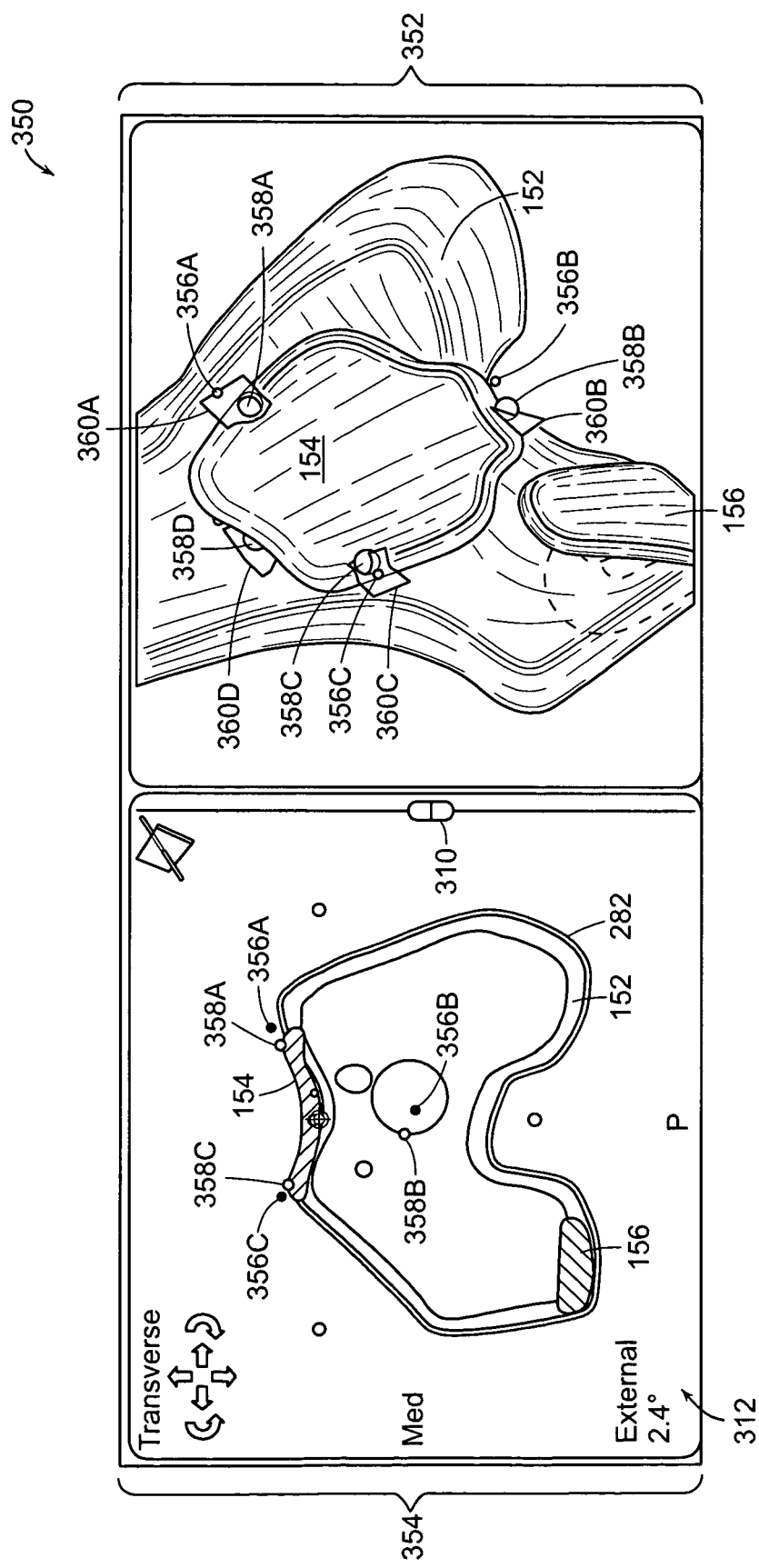
FIG. 6 illustrates a split display including cartilage areas along a representation of a bone.

FIG. 6 illustrates a split display 350 including cartilage areas along a representation of a bone. The split display 350 includes a three-dimensional display 352 and a two-dimensional display 354. The three-dimensional display 352 includes the representation of the femur 152, the representation of the patello-femoral implant component 154, and the representation of the medial implant component 156. The three-dimensional display 352 includes cartilage points 356A, 356B, and 356C (collectively, cartilage points 356). The three-dimensional display 352 includes control points 358A, 358B, 358C and 358D (collectively, control points 358). The three-dimensional display 352 includes areas representing cartilage 360A, 360B, 360C and 360D (collectively, areas representing cartilage 360).

The two-dimensional display 354 includes the representation of the femur 152, the representation of the patello-femoral implant component 154, and the representation of the medial implant component 156. The two-dimensional display 354 includes cartilage points 356A, 356B, and 356C. The three-dimensional display 352 includes control points 358A, 358B, and 358C. The two-dimensional display includes a slider 310 and a change indicator 312 as discussed above with reference to FIG. 5.

Figure 7:
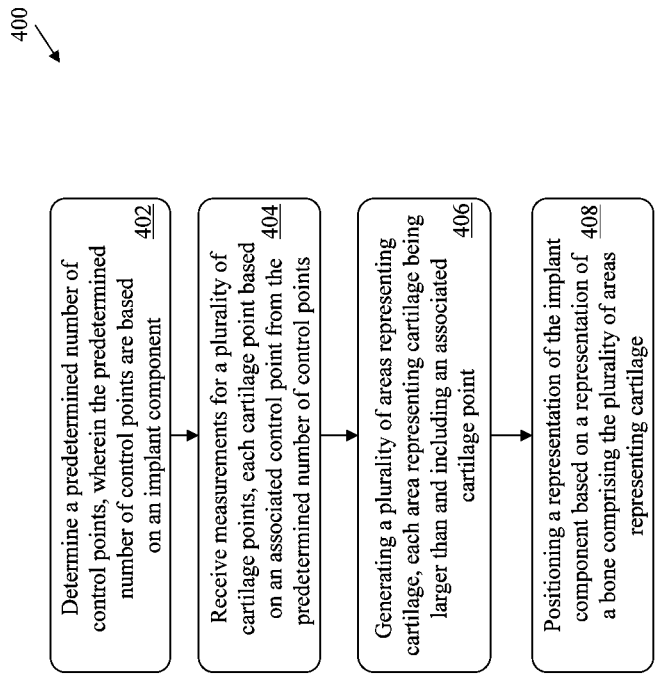
FIG. 7 illustrates an exemplary method for positioning an implant component based on areas representing cartilage.

FIG. 7 illustrates an exemplary process 400 for positioning an implant component based on areas representing cartilage, using FIG. 6 as an example. The representation of the femur 152 can be generated from a CT scan. In some examples, a CT scan only matches the surface of the bone, but not the surface of articular cartilage. In some embodiments, the surface of the cartilage can be used to determine an optimal placement of an implant component. For example, the thickness of articular cartilage can be determined at critical places on the bone and used to position the implant component. In some embodiments, a cartilage surface can be generated by capturing (e.g., with an optical camera) the tip positions of a tracked probe which is dragged over the cartilage surface. The cartilage surface generated from the captured points can be used to manually or automatically position the implant component to the resulting surface. For example, to manually position the implant component, the system 100 can display a representation of the cartilage surface, and the user can manipulate the representation of the implant component to achieve the desired placement of the implant component surface relative to the cartilage surface. In this example, a sufficient number of points are captured by the probe to generate a representation of the cartilage surface. Advantageously, cartilage thickness of the bone can be estimated over a region by lifting a patch of the bone model to the estimated position. A predetermined number of control points 358 are determined (402) based on the representation of the patello-femoral implant component 154. The control points can be, for example, along exterior edges of the implant component, at critical places of the implant component, at the most exterior points of the component, any other location along the implant component, or outside or off the implant component surface but defined in the coordinate space of the implant component. In this example, four control points are used. In other examples, any number of control points can be used. Measurements and/or calculations of the thickness and/or direction of cartilage points 356 are received (404), where each cartilage point is tied to an associated control point from the control points 358. For example, cartilage point 356A is measured in proximity to control point 358A. Areas representing cartilage 360 are generated (406), wherein each area representing cartilage is larger than and projects to the associated control point. For example, the area representing cartilage 360A is larger than and projects to control point 358A. For example, the system can assume the cartilage is about the same depth within a 10 mm diameter circle from a measurement point. Measuring one point allows an area of a 10 mm diameter to be estimated on the bone model, rather than calculating the entire cartilage area over the bone. Taking cartilage surface measurements at predetermined locations near the control points allows the locations to coincide with the control points on the implant component, making other cartilage portions on the bone irrelevant. A representation of the patello-femoral implant component 154 is positioned (408) based on the representation of the femur 152. The representation of the femur 152 includes the areas representing cartilage 360.

In some examples, the areas representing cartilage 360 are formed from adjusted points on the representation of the femur 152. Forming the areas representing cartilage 360 on the representation of the femur 152 causes protrusions along the representation of the femur 152. The control points 358 on the representation of the patello-femoral implant component 154 can be used to reposition the patello-femoral implant component 154 in the coordinate space of the implant system (e.g., the coordinate space of the representation of the femur 152). For example, the patello-femoral implant component 154 can be repositioned away from the representation of the femur 152 so that the patello-femoral implant component 154 is positioned adjacent to the representations of the areas representing cartilage 360. Because the entire cartilage surface was not generated along the representation of the femur 152, this can result in a gap between the patello-femoral implant component 154 and the representation of the femur 152 where the patello-femoral implant component 154 is not adjacent to the areas representing cartilage 360. In this case, points can be picked on the bone itself.

Figure 8:
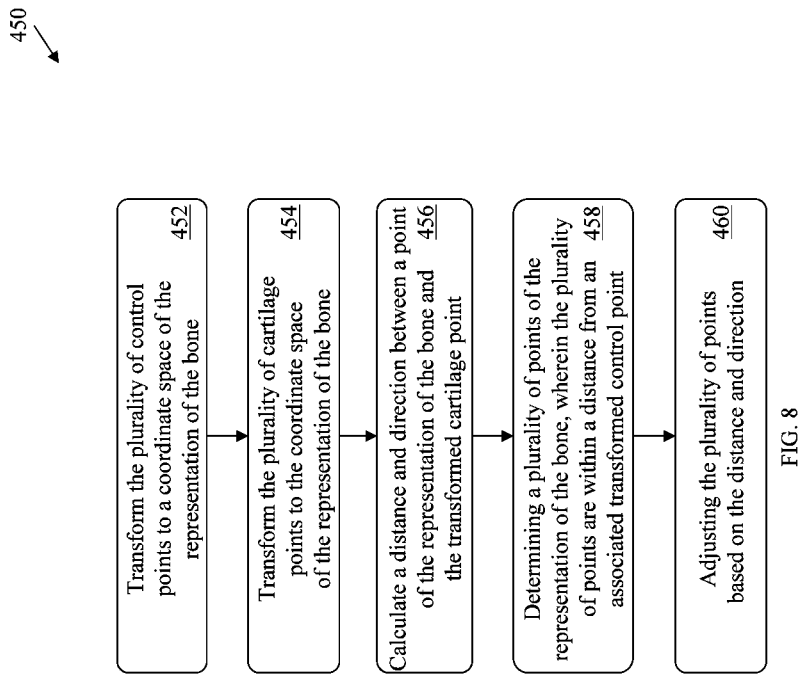
FIG. 8 illustrates an exemplary method for estimating areas representing cartilage.
Figure 9B:
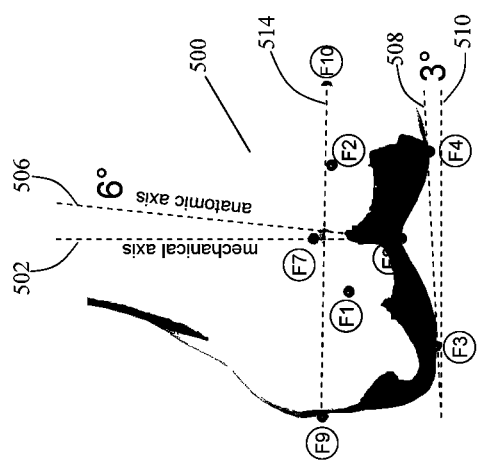
FIGS. 9A-9D illustrate bone points on a femur for implant planning.
Figure 9A:
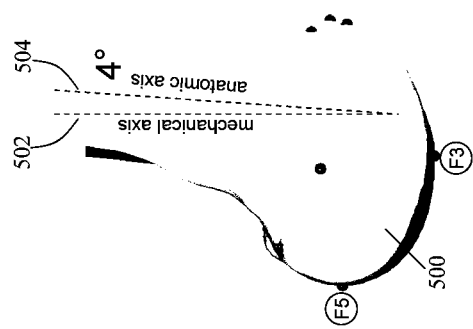
Figure 9D:
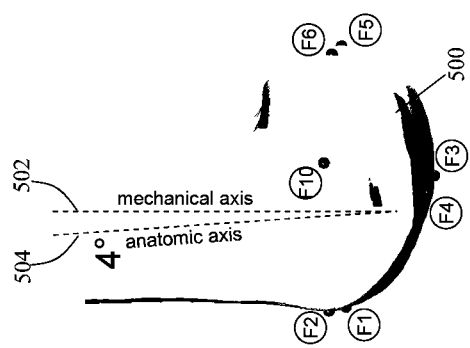
Figure 9C:
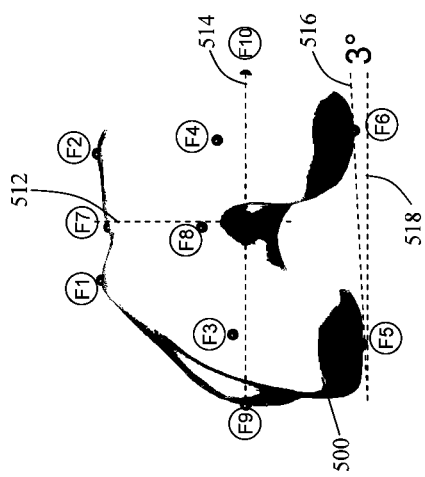

FIG. 8 illustrates an exemplary process (450) for estimating areas representing cartilage. The surface of the cartilage is estimated at selected points by taking one cartilage measurement at locations on the patient's cartilage that correspond to each control point and using the resulting distance and direction from the representation of the bone to create an area representing cartilage using the representation of the bone and the resulting offset. Using, for example, a tracked probe, an operator captures cartilage points 356 on the patient in proximity to each of the control points 358 of the selected implant (e.g., the representation of the patello-femoral implant 154). Take:

$C_B$=the coordinate space of the bone model;
$C_I$=the coordinate space of the implant;
$C_P$=the coordinate space of the patient;
$T_I$=the transformation from CI to CB; and
$T_P$=the transformation from CP to CB.

To estimate an area representing cartilage 360 at the position of each control point 358 relative to the representation of the femur 152, each cartilage point 356 is transformed (452) to $C_B$ using $T_P$. Each control point 358 is transformed (454) to $C_B$ using $T_I$. The system 100 determines the closest point on the representation of the femur 152 to the transformed cartilage point 356. The system 100 calculates (456) the distance and direction from the closest point from the representation of the femur 152 to the transformed cartilage point 356. In some embodiments, the system 100 calculates a direction between a closest point of the representation of the femur 152 to an associated transformed control point and uses the distance (cartilage thickness) of the transformed cartilage point 356 from the representation of the femur 152. The system 100 determines (458) a plurality of points of the representation of the femur 152 that are within a distance from the associated transformed control point. The plurality of points from the representation of the femur 152 are adjusted (460) based on the distance and direction.

The three-dimensional representation of the femur 152 can be made up of geometrical shapes. For example, if the representation of the femur 152 is created with triangles, a group of triangles on the representation of the femur 152 which are closest to the transformed control point are determined. Each vertex in the group is adjusted using the cartilage distance and direction to form an area representing cartilage 360. The geometrical shapes of three-dimensional representation of the femur 152 can be a set of polygons. Each of the plurality of points of the representation of the femur 152 can correspond to a set of polygons from the superset of polygons that make up the representation of the femur 152. The transformed control points can be registered to the closest points on the areas representing cartilage 360 using, for example, a paired-point registration algorithm. Geometrical shapes can be used to represent any component (e.g., patello-femoral implant component 154, medial implant component 156, and/or lateral implant component 158).

The final registration to the areas representing cartilage 360 can be suitably constrained (e.g., around an axis) to automatically adjust the position of one implant relative to another. For example, if the representation of the patello-femoral implant component 154 is adjusted based on the generated areas representing cartilage 360, the representation of the medial implant component 156 can be automatically adjusted to coincide with the adjustment of the representation of the patello-femoral implant component 154. Advantageously, all implant components can be adjusted to account for the generation of areas representing cartilage around one implant component.

FIGS. 9A-9D illustrate bone points along a femur 500 for implant planning. The femur includes a mechanical axis 502, anatomic axis 504 at 4° from the mechanical axis 502, and anatomic axis 506 at 6° from the mechanical axis 502. Bone 500 includes bone points F1 through F10. Bone points F1-F10 can be extreme points of the femur 500. The bone points can represent, for example:

F1—Most anterior medial point;
F2—Most anterior lateral point;
F3—Most distal medial point;
F4—Most distal lateral point;
F5—Most posterior medial point;
F6—Most posterior lateral point;
F7—Most anterior trochlear groove;
F8—Most distal trochlear groove;
F9—Medial epicondyle; and
F10—Lateral epicondyle.

The femur 500 can also include points F14 and F15 (not shown), where F14 is at the midpoint between F1 and F5, and point F15 is at the midpoint between F2 and F6. Bone points F3 and F4 make up the distal condylar axis (DCA) 508. The DCA 508 is approximately 3° from horizontal 510. F7 and F8 represent the Anterior-posterior axis (AP axis) 512. F9 and F10 represent the Transepicondylar axis (TEA) 514. The TEA 514 is perpendicular to the AP axis 512. F5 and F6 make up the posterior condylar axis (PCA) 516. The PCA 516 is approximately 3° from a line 518 that is parallel to the TEA 514.

Figure 10A:
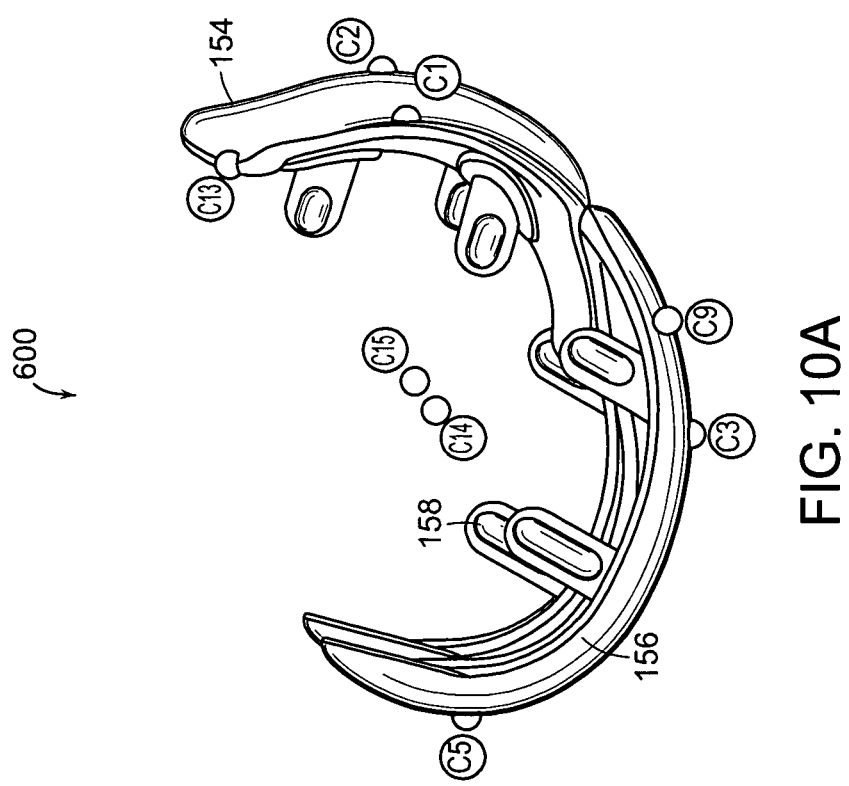
Figure 10C:
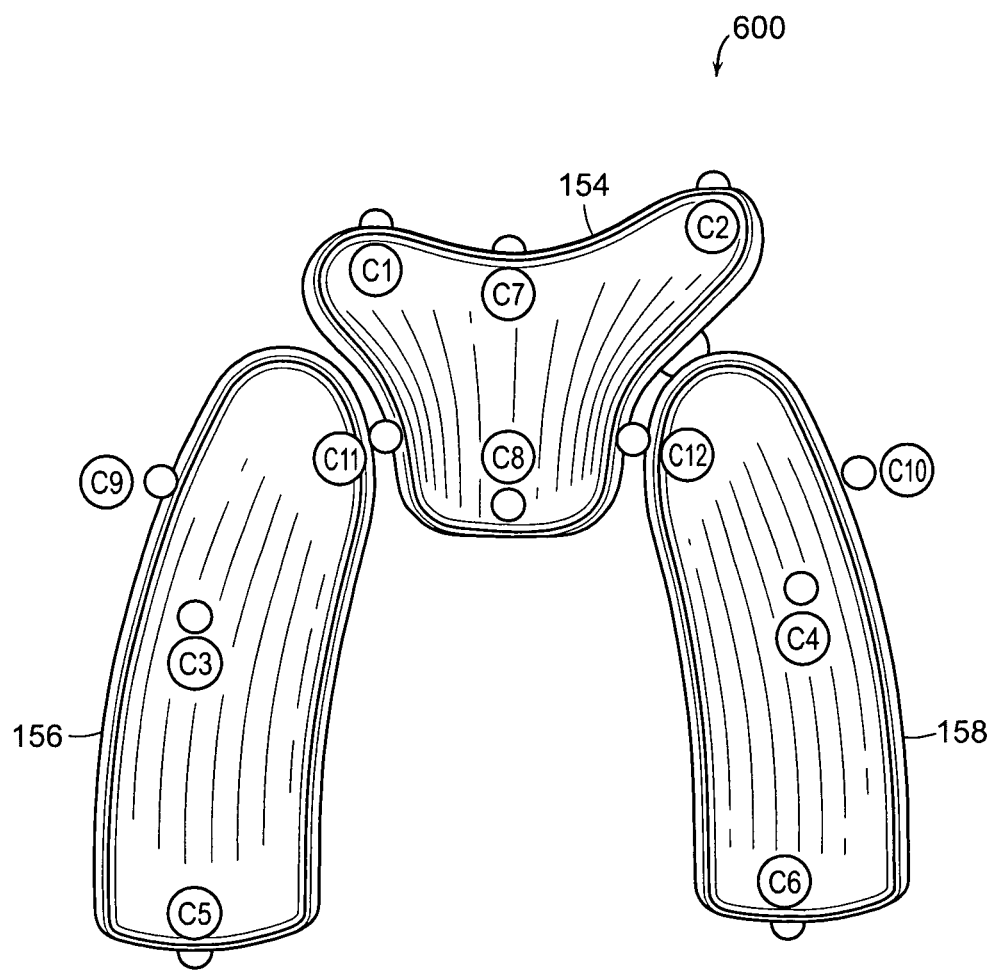

FIGS. 10A-10C illustrate implant points on implant components of a multiple component implant 600 (i.e., the patello-femoral implant component 154, the medial implant component 156, and the lateral implant component 158) for implant planning. The implant points include points C1-C15. The implant points can represent, for example:

C1—Most anterior medial point;
C2—Most anterior lateral point;
C3—Most distal medial point;
C4—Most distal lateral point;
C5—Most posterior medial point;
C6—Most posterior lateral point;
C7—Most anterior trochlear groove;
C8—Most distal trochlear groove;
C9—Center of medial transition arc;
C10—Center of lateral transition arc;
C11—Medial transition location;
C12—Lateral transition location;
C13—Superior transition location;
C14—Midpoint between points C1 and C5; and
C15—Midpoint between points C2 and C6.

Point C9 lies on the primary articular surface with the same X and Y value as the internal edge arc center of the medial femoral implant component (i.e., the medial implant component 156). C10 lies on the primary articular surface with the same X and Y value as the internal edge arc center of the lateral femoral implant component (i.e., the lateral implant component 158). C11 lies on the primary articular surface, the midplane between the lateral edge of the medial femoral implant component and the medial edge of the patello-femoral implant component 154, and the midplane between the anterior tip of the medial femoral implant component and the posterior tip of the patello-femoral implant component 154. C11 can serve as the location for upsizing/downsizing femoral or patello-femoral implant components. C12 lies on the primary articular surface, the midplane between the medial edge of the lateral femoral implant component and the lateral edge of the patello-femoral implant component 154, and the midplane between the anterior tip of the lateral femoral implant component and the posterior tip of the patello-femoral implant component 154. C12 can also serve as the location for upsizing/downsizing femoral or patello-femoral components. C13 lies on a surface that is midway between the articular surface and the backside surface (1.5 mm offset from primary articular surface), on the outer profile of the patello-femoral implant component 154, on the trochlear groove pathway. C14 is the midpoint between the most anterior and most posterior medial points. C14 can be used in pre-operative planning. C15 is the midpoint between the most anterior and most posterior lateral points. C15 can be used in pre-operative planning.

Figure 11B:
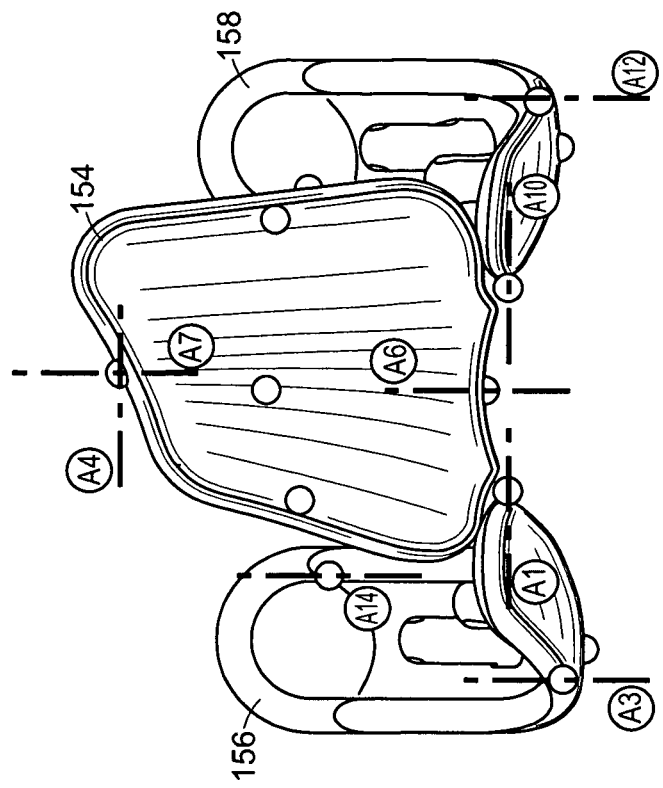
FIGS. 11A-11C illustrate implant component axes relative to implant components of a multiple component implant for implant planning.
Figure 11A:
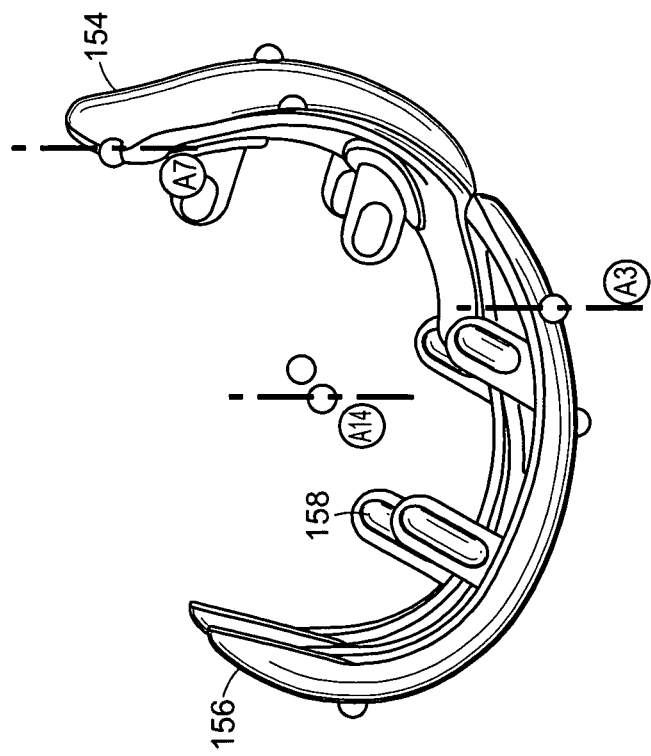
Figure 11C:
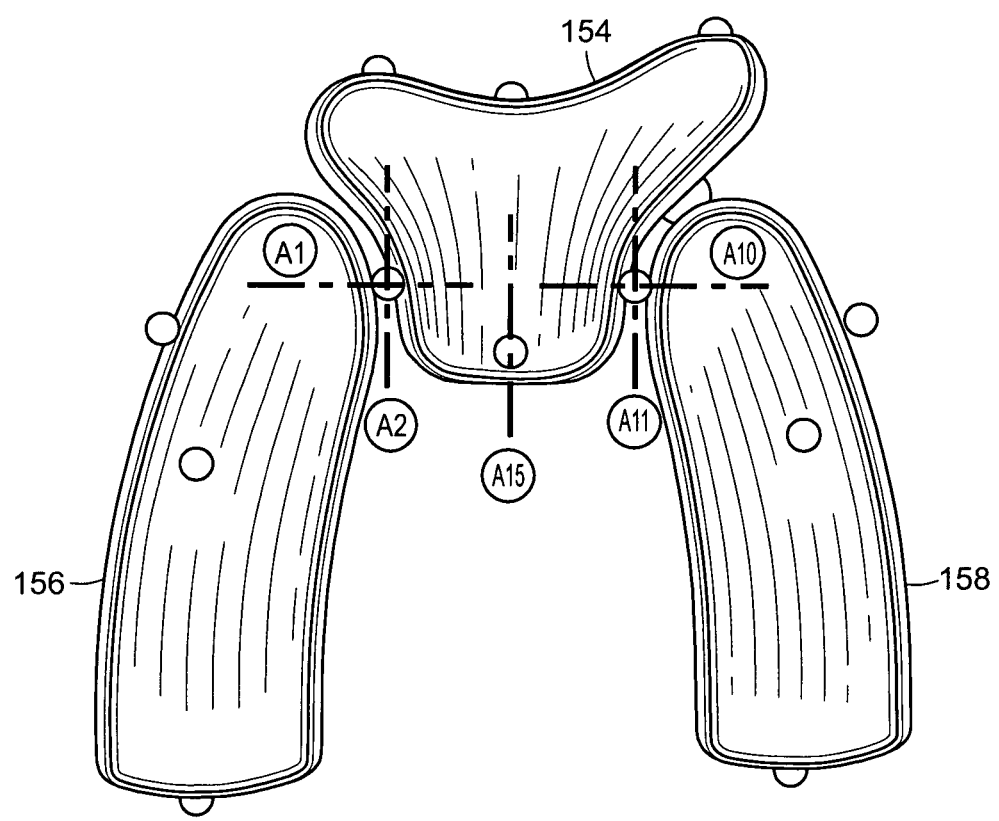

FIGS. 11A-11C illustrate implant component axes relative to the implant components of a multiple component implant 600 (i.e., the patello-femoral implant component 154, the medial implant component 156, and the lateral implant component 158) for implant planning. The axes can include axes A1-A15, which can represent, for example:

A1—Medial medial-lateral (ML) axis (x-axis) through point C11 (e.g., flexion/extension);
A2—Medial anterior-posterior (AP) axis (y-axis) through point C11 (e.g., varus/valgus);
A3—Medial superior-inferior (SI) axis (z-axis) through point C9 (e.g., internal/external);
A4—Patello-femoral (PFJ) superior ML axis (x-axis) through point C13 (e.g., flexion/extension);
A5—Axis through points C11 and C13;
A6—SI axis (z-axis) through point C8 (e.g., internal/external);
A7—SI axis (z-axis) through point C13 (e.g., internal/external);
A8—SI axis (z-axis) through midpoint of C8 and C13 (e.g., internal/external);
A9—Axis through points C8 and C13;
A10—Lateral ML axis (x-axis) through point C12 (e.g., flexion/extension);
A11—Lateral AP axis (y-axis) through point C12 (e.g., varus/valgus);
A12—Lateral SI axis (z-axis) through point C10 (e.g., internal/external);
A13—Axis through points C12 and C13;
A14—SI axis (z-axis) through C14 (e.g., internal/external); and
A15—AP axis (y-axis) through point C8 (e.g., varus/valgus).

For pre-operation planning, cartilage points can be assumed. These cartilage points can include:

F1'—Most anterior medial point+1 mm in the Y direction;
F2'—Most anterior lateral point+1 mm in the Y direction;
F3'—Most distal medial point−2 mm in the Z direction;
F4'—Most distal lateral point−2 mm in the Z direction;
F5'—Most posterior medial point−2 mm in the Y direction;

F6'—Most posterior lateral point−2 mm in the Y direction;
F7'—Most anterior trochlear groove+2 mm in the Y direction;
F8'—Most distal trochlear groove−2 mm in the Z direction;
F14'—Midpoint between F1' and F5'; and
F15'—Midpoint between F2' and F6'.

Mapped transition points can be taken (e.g., manually with a probe). Any number of mapped transition points can be used. These points, for a femur for example, can include:

M1—Most anterior medial point mapped on cartilage near C1;
M2—Most anterior lateral point mapped on cartilage near C2;
M7—Most anterior trochlear point mapped on cartilage near C7;
M8—Most distal trochlear groove mapped on cartilage near C8;
M11—Medial transition mapped on cartilage near C11;
M12—Lateral transition mapped on cartilage near C12; and
M13—Superior transition mapped on bone near C13.

In some embodiments, a tibial onlay or inlay implant component (e.g., an articular surface) can be calculated. The tibial onlay or inlay implant component can include, for example:

P000—a poly centroid at 0° flexion mapped into femoral implant space;
P090—a poly centroid at 90° flexion mapped into femoral implant space; and
PXXX—any other poly centroid at XXX ° flexion mapped into femoral implant space.

Such onlays or inlays can provide, for example, a relationship between the tibia and the femur. Advantageously, this can prevent positioning of the implant components in a way that adversely affects the tibia (e.g., causing excessive tightening).

Preoperative Planning

The following is one example of preoperative planning. Preoperative planning can include acquiring the hip center and ankle center of the patient. Bounding box bone landmarks (e.g., for the femur and tibia, such as points F1-F10) are acquired. The bones of interest are orientated, and the bounding box bone landmarks can be re-acquired based on the final orientation. A proper implant size is selected from the variety of sizes available to the system 100. In some embodiments, a proper implant size is calculated by computing the anterior-posterior (AP) distance as the ΔY between points F1' and F5'. This will be described for a three component implant. A three component implant may be, for example, a tricompartmental implant that includes an implant component for each of the three compartments of the joint (e.g., the medial compartment, the lateral compartment, and the patello-femoral compartment). For example, a tricompartmental implant can include the patello-femoral implant component, the medial femoral implant component, and the lateral femoral implant component. A three component implant may also be an implant that includes three components that are implanted in one or more compartments of the joint (e.g., the medial compartment, the lateral compartment, and/or the patello-femoral compartment). For example, the patello-femoral implant component can be split into three segmented components that are each implanted in the patello-femoral compartment of the joint. In another example, the patello-femoral implant component 154 could be split into two segmented components that are used in combination with one other implant component (e.g., the medial or lateral femoral implant component). In this example, the three component implant is a tricompartmental implant that includes the patello-femoral implant component (e.g., represented by representation 154), the medial implant component (e.g., represented by representation 156), and the lateral implant component (e.g., represented by representation 158). For the tricompartmental implant, a size is selected that best matches this distance (ΔY between points C1 and C5) by finding the size that has the minimum difference. The system 100 displays the three component implant, in this example, a tricompartmental implant.

A best fit is determined for the tricompartmental implant to points F1' through F8'. In some embodiments, a best fit is found by performing a number of steps: (1) translate the tricompartmental implant such that C14 is at the same location as F14', (2) rotate the tricompartmental implant about axis A14 until C15 has the same y-value as F15', (3) translate in the medial-lateral (ML) direction until the midpoint of C1-C2 has the same x-value as the midpoint of F1'-F2' (or until C8 has same x-value as F8'), (4) translate in the superior-inferior (SI) direction until C8 has the same z-value as F8', (5) rotate about axis A15 until ΔZ between points C3 and F3' is equal to ΔZ between points C4 and F4', (6) repeat until changes are insignificant.

Intraoperative Planning

The following is an exemplary example of steps that can be performed during intraoperative planning. During the operation, the patient's bone is registered, as described, for example, in U.S. Patent Publication 2006/0142657, published Jun. 29, 2006, which is hereby incorporated by reference herein in its entirety. Bone poses can be captured, for example, at 0°, 90°, and other angles. Transition region points are captured (e.g., medial cartilage transition, lateral cartilage transition, superior bone transition, and/or the like).

An implant size is calculated for the patient. The system 100 computes the AP distance by, for example, computing the ΔY between points M13 and P090. The system 100 selects the tricompartmental implant size by, for example, determining the tricompartmental implant size that has a minimum difference from the ΔY between points C5 and C13. The system 100 can display a representation of the selected tricompartmental implant (e.g., through display 108 of FIG. 1).

The system 100 fits the implant to pose capture and transition region acquisition points.

For example, the system 100 or a user can move (e.g., rotate, translate, etc.) the patello-femoral implant component (e.g., the representation 154) to a desired orientation and location. In some examples, the femoral components (e.g., the representations 156, 158) move linked to the patello-femoral implant component. In some examples, the patello-femoral implant component can be automatically fit to the bone with movements (e.g., rotations, translations, etc.) to match the patello-femoral implant component to the mapped points (e.g., the mapped transition points M1, M2, M7, M8, M11, M12, M13).

Other computer operations can be performed, such as a fit to the femoral condyle of the femur or a fit to all portions of the bone. This will be described for a two component implant. A two component implant may be, for example, a bicompartmental implant that includes an implant component for two of the three compartments of the joint (e.g., the medial compartment, the lateral compartment, the patello-femoral compartment). For example, a bicompartmental implant can include the patello-femoral implant component and either the medial femoral implant component or the lateral femoral implant component. In another example, a bicompartmental implant can include the medial and lateral femoral implant components. A two component implant may also be an implant that includes two components that are implanted in one compartment of the joint (e.g., the medial compartment, the lateral compartment, or the patello-femoral compartment). For example, the patello-femoral implant component can be split into two segmented components that are each implanted in the patello-femoral compartment of the joint. In this example, the two component implant is a bicompartmental implant that includes the patello-femoral implant component (e.g., the representation 154) and the medial implant component (e.g., the representation 156). The bicompartmental implant AP can be moved so that C13 has the same y-value as M13. The bicompartmental implant SI can be moved so that C8 has the same z-value as M8. The femoral component internal-external (IE) can be rotated about axis A3 until the x-value of C5 matches the x-value of P090. The femoral component flexion-extension (FE) can be rotated about axis A1 until the z-value of C3 matches the z-value of P000.

The posterior gap can be calculated and/or displayed by measuring the ΔY between points C5 and P090. The system 100 can determine the fit (e.g., if there is a gap/loose or if there is an overlap/tight). If the system 100 determines the posterior gap is loose, the length can be increased. To increase length, for example, the bicompartmental implant can be flexed about axis A4. The system 100 can determine the rotation angle value for each size that approximately yields a 0.5 mm length increase. To decrease length, the bicompartmental implant can be extended about axis A4. The system 100 can determine the rotation angle value for each size that approximately yields a 0.5 mm length increase. The user can, for example, click the display to adjust the length by a predetermined amount (e.g., increase/decrease the length by 0.5 mm). Any number of these steps can be repeated one or more times to achieve a desired posterior gap.

Adjustments can be made to the femoral component (e.g., the medial implant component 156 or the lateral implant component 158). For example, the varus/valgus can be adjusted to fit the bone, the flexion/extension can be adjusted to change the extension gap, and any other adjustment can be made. To increase or decrease a size of the implant system or implant components (e.g., the femoral/patello-femoral), a new component can be placed in at C11. To upsize and/or downsize the femoral implant component when, for example, the bone has already been resected to include peg holes to receive the pegs (or posts) on the back of the femoral implant component and a pocket to receive the body of the femoral implant component, the next sized femoral implant component needs can be placed into position at the peg axes at a predetermined depth. Tibial inlay and/or onlay implant component articular surfaces can be matched. The system 100 can calculate the angle change necessary to increase and/or decrease the size of the bicompartmental implant. The tricompartmental implant can be automatically fit to the bone, pose, transition, and/or the like. While the above example was described with reference to the medial femoral implant component, those skilled in the art can appreciate these systems and methods can be extended to any multiple implant component system.

Figure 12:
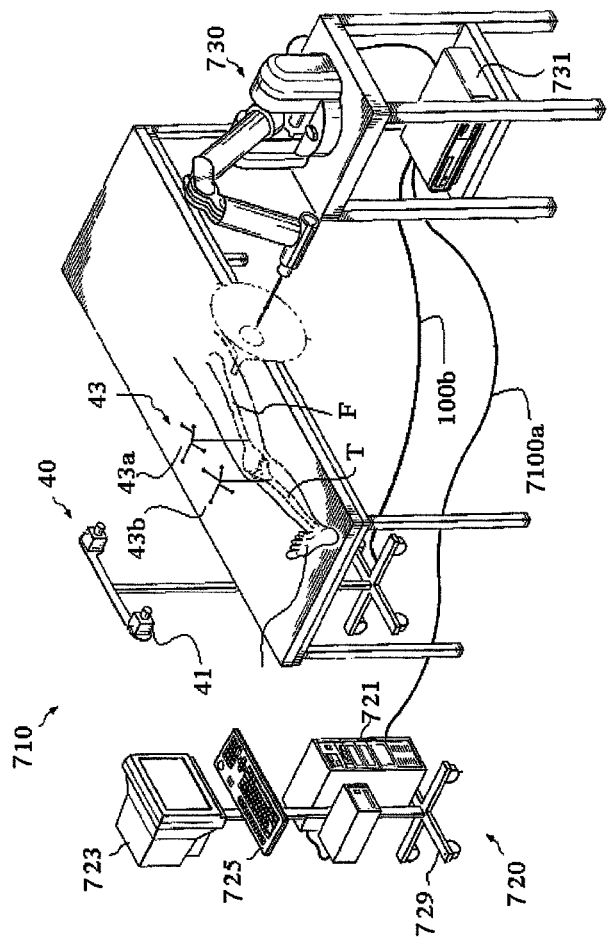
FIG. 12 shows an embodiment of an exemplary surgical computer system for implant planning using constraints and/or areas representing cartilage.

FIG. 12 shows an embodiment of an exemplary surgical system 710 in which the techniques described above can be implemented. Such an exemplary system is described in detail, for example, in U.S. Patent Publication 2006/0142657, published Jun. 29, 2006, which is hereby incorporated by reference herein in its entirety. The surgical system 710 includes a computing system 720, a haptic device 730, and a navigation system 40. In operation, the surgical system 710 enables comprehensive, intraoperative surgical planning. The surgical system 710 also provides haptic guidance to a user (e.g., a surgeon) and/or limits the user's manipulation of the haptic device 730 as the user performs a surgical procedure. Although included for completeness in the illustrated embodiment, the haptic device 730 and its associated hardware and software is not necessary to perform the techniques described herein.

The computing system 720 includes hardware and software apparatus for operation and control of the surgical system 710. Such hardware and/or software apparatus is configured to enable the system 710 to perform the techniques described herein. In FIG. 12, the computing system 720 includes a computer 721, a display device 723, and an input device 725. The computing system 720 may also include a cart 729.

The computer 721 may be any known computing system but is preferably a programmable, processor-based system. For example, the computer 721 may include a microprocessor, a hard drive, random access memory (RAM), read only memory (ROM), input/output (I/O) circuitry, and any other well-known computer component. The computer 721 is preferably adapted for use with various types of storage devices (persistent and removable), such as, for example, a portable drive, magnetic storage (e.g., a floppy disk), solid state storage (e.g., a flash memory card), optical storage (e.g., a compact disc or CD), and/or network/Internet storage. The computer 721 may comprise one or more computers, including, for example, a personal computer (e.g., an IBM-PC compatible computer) or a workstation (e.g., a SUN or Silicon Graphics workstation) operating under a Windows, MS-DOS, UNIX, or other suitable operating system and preferably includes a graphical user interface (GUI).

The display device 723 is a visual interface between the computing system 720 and the user. The display device 723 is connected to the computer 721 and may be any device suitable for displaying text, images, graphics, and/or other visual output. For example, the display device 723 may include a standard display screen (e.g., LCD, CRT, plasma, etc.), a touch screen, a wearable display (e.g., eyewear such as glasses or goggles), a projection display, a head-mounted display, a holographic display, and/or any other visual output device. The display device 723 may be disposed on or near the computer 721 (e.g., on the cart 729 as shown in FIG. 12) or may be remote from the computer 721 (e.g., mounted on a wall of an operating room or other location suitable for viewing by the user). The display device 723 is preferably adjustable so that the user can position/reposition the display device 723 as needed during a surgical procedure. For example, the display device 723 may be disposed on an adjustable arm (not shown) that is connected to the cart 729 or to any other location well-suited for ease of viewing by the user.

The display device 723 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), constraint data (e.g., axes, articular surfaces, etc.), representations of implant components, digital or video images, registration information, calibration information, patient data, user data, measurement data, software menus, selection buttons, status information, and the like. In some examples, the display device 723 displays the two dimensional and/or three dimensional displays as illustrated in FIGS. 2, 4A-4B, 5, and 6.

In addition to the display device 723, the computing system 720 may include an acoustic device (not shown) for providing audible feedback to the user. The acoustic device is connected to the computer 721 and may be any known device for producing sound. For example, the acoustic device may comprise speakers and a sound card, a motherboard with integrated audio support, and/or an external sound controller. In operation, the acoustic device may be adapted to convey information to the user. For example, the computer 721 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a beep to indicate that a surgical cutting tool is nearing a critical portion of soft tissue.

The input device 725 of the computing system 720 enables the user to communicate with the surgical system 710. The input device 725 is connected to the computer 721 and may include any device enabling a user to provide input to a computer. For example, the input device 725 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick. For example, the input device 725 allows a user to move one or more components displayed on display device 723 based on one or more constraints, as described above, for planning the implant installation.

The computing system 720 is coupled to a computing device 731 of the haptic device 730 via an interface 7100a and to the navigation system 40 via an interface 100b. Interfaces 7100a and 100b can include a physical interface and a software interface. The physical interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system). The software interface may be resident on the computer 721, the computing device 731, and/or the navigation system 40. In some embodiments, the computer 721 and the computing device 731 are the same computing device.

The surgical system 710 has additional features as described in U.S. patent application Ser. No. 11/963,547, filed Dec. 21, 2007, which is hereby incorporated by reference herein in its entirety. In some examples, the surgical system 710 allows a user to plan the installation of a multiple component implant in a patient using the computing system 720. The user, for example, uses the input device 725 to position (e.g., rotate, translate, shift, etc.) one or more components of a multiple component implant based on one or more constraints to properly fit the unique anatomy of the patient. The planning procedure, once completed, is transmitted to and/or used by the haptic device 730 via interface 7100a to assist a surgeon during the bone preparation and implant installation procedure.

In some examples, the haptic device 730 is the Tactile Guidance System™ (TGS™) manufactured by MAKO Surgical Corp., which is used to prepare the surface of the patient's bone for insertion of the implant system. The haptic device 730 provides haptic (or tactile) guidance to guide the surgeon during a surgical procedure. As described in U.S. Patent Publication 2006/0142657, published Jun. 29, 2006, which is hereby incorporated by reference herein in its entirety, the haptic device is an interactive surgical robotic arm that holds a surgical tool (e.g., a surgical burr) and is manipulated by the surgeon to perform a procedure on the patient, such as cutting a surface of a bone in preparation for implant installation. As the surgeon manipulates the robotic arm to move the tool and sculpt the bone, the haptic device 730 guides the surgeon by providing force feedback that constrains the tool from penetrating a virtual boundary.

For example, the surgical tool is coupled to the robotic arm and registered to the patient's anatomy. The surgeon operates the tool by manipulating the robotic arm to move the tool and perform the cutting operation. As the surgeon cuts, an optical camera 41 of the navigation system 40 tracks the location of the tool and the patient's anatomy. The patient's anatomy can be tracked, for example, by attaching a tracking array 43a to the patient's femur F and a tracking array 43b to the patient's tibia T, as shown in FIG. 12. The tracking arrays 43a, 43b are detectable by the optical camera 41. In most cases, the haptic device 730 allows the surgeon to freely move the tool in the workspace. However, when the tool is in proximity to the virtual boundary (which is also registered to the patient's anatomy), the haptic device 730 controls the haptic device to provide haptic guidance (e.g., force feedback) that tends to constrain the surgeon from penetrating the virtual boundary with the tool.

The virtual boundary may represent, for example, a cutting boundary defining a region of bone to be removed or a virtual pathway for guiding the surgical tool to a surgical site without contacting critical anatomical structures. The virtual boundary may be defined by a haptic object (e.g., one or more haptic objects, as described below in further detail), and the haptic guidance may be in the form of force feedback (i.e., force and/or torque) that is mapped to the haptic object and experienced by the surgeon as resistance to further tool movement in the direction of the virtual boundary. Thus, the surgeon may feel the sensation that the tool has encountered a physical object, such as a wall. In this manner, the virtual boundary functions as a highly accurate virtual cutting guide. For example, the virtual boundary can represent a region of cartilage and/or bone to be removed for properly fitting the medial, lateral, and patello-femoral implant components to the patient's femur as planned through the implant planning procedure described above. Such virtual boundaries can help to ensure the efficient and accurate removal of portions of a patient's anatomy to accurately fit implant components based on a customized implant planning for the patient. This also ensures that the actual placement of the implant components meets the constraints that were used in planning the placement of each of the physically separate implant components.

In some examples, the haptic device 730 includes a visual display (e.g., the display device 723 shown in FIG. 12) showing the amount of bone removed during the cutting operation. Because the haptic device 730 utilizes tactile force feedback, the haptic device 730 can supplement or replace direct visualization of the surgical site and enhance the surgeon's natural tactile sense and physical dexterity. Guidance from the haptic device 730 coupled with computer aided surgery (CAS), enables the surgeon to actively and accurately control surgical actions (e.g., bone cutting) to achieve the tolerances and complex bone resection shapes that enable optimal and customized installation of implants.

In addition to bone preparation, a CAS system enables the surgeon to customize the placement of the implant components to construct a prosthetic device tailored to the specific needs of the patient based on the patient's unique anatomy, ligament stability, kinematics, and/or disease state. Implant planning may be accomplished preoperatively or intraoperatively and may be evaluated and adjusted in real time during execution of the surgical procedure. In a preferred embodiment, implant planning is accomplished using the surgical system 710. For example, as described above, the surgeon may use the surgical planning features of the computing system 720 to plan the placement of representations of each implant component relative to a preoperative CT image (or other image or model of the anatomy). The software enables the surgeon to view the placement of each component relative to the anatomy (e.g., bone, articular cartilage surfaces, and/or the like) and to other components, as described, for example, in U.S. Patent Publication 2006/0142657, published Jun. 29, 2006, which is hereby incorporated by reference herein in its entirety. Further, the software enables the surgeon to view constraints associated with the placement of each component (e.g., articular surfaces, axes of constraint, and/or the like). The software may also be configured to illustrate how the components will interact as the joint moves through a range of motion. Based on the component placement selected by the surgeon, the haptic device 730 software generates one or more haptic objects, which create one or more virtual boundaries representing, for example, a portion of bone to be removed or critical anatomy to be avoided based at least in part on the placement of the implant components. During surgery, the haptic object is registered to the patient's anatomy. By providing force feedback, the haptic device 730 enables the surgeon to interact with the haptic object in the virtual environment. In this manner, the haptic device 730 haptically guides the surgeon during bone preparation to sculpt or contour the appropriate location of the bone so that a shape of the bone substantially conforms to a shape of a mating surface of a component of the multiple component implant. For example, a haptic object can be created to represent the portion of the bone and/or cartilage area to be removed for implanting the medial femoral implant component (e.g., represented by the representation 156).

In a preferred embodiment, the haptic device 730 is used by the surgeon to preoperatively plan implant placement using computer simulation tools to determine whether the preoperative plan will result in the desired clinical results (e.g., using constraints). Then, during surgery, the surgeon may query the soft tissue and ligaments as the joint is moved through a range of motion using appropriate instrumentation and sensors as is well known. This information may be combined with the computer simulation information of the haptic device 730 to adjust the implant planning and/or suggest to the surgeon potential changes and adjustments to implant placement that may achieve the desired clinical outcomes.

The above-described systems and methods can be implemented in digital electronic circuitry, in computer hardware, firmware, and/or software. The implementation can be as a computer program product (i.e., a computer program tangibly embodied in an information carrier). The implementation can, for example, be in a machine-readable storage device, for execution by, or to control the operation of, a data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer available from Microsoft Corporation, Mozilla® Firefox available from Mozilla Corporation). The mobile computing device includes, for example, a personal digital assistant (PDA).

Comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A surgical planning computerized method comprising:
   determining, using a computer programmed to perform the steps of the method, a predetermined number of control points for generating a predetermined number of areas representing cartilage, wherein the predetermined number of control points are associated with specified locations on a first implant component of a multiple-component implant;
   receiving measurements corresponding to a plurality of measured cartilage points, wherein each cartilage point is based on an associated control point from the predetermined number of control points;
   generating a plurality of areas representing cartilage, based on and in proximity to each cartilage point, wherein each area representing cartilage is associated with a control point, and wherein each area representing cartilage is larger than and projects to an associated control point from the predetermined number of control points;
   selecting a properly-sized multiple-component implant by computing a distance between two or more measured cartilage points and selecting a multiple-component implant having a distance between the two or more associated control points of the first implant that best matches the computed distance between the two or more cartilage points;
   positioning a representation of a first implant component of the properly-sized multiple-component implant by aligning the control points for the first implant with the associated measured cartilage points;
   automatically positioning a representation of a second implant component of the properly-sized multiple-component implant based on the position of the representation of the first implant component; and
   generating at least one virtual cutting boundary based on the position of the representation of a first implant component and the position of the representation of the second implant component, wherein the virtual cutting boundary is configured to provide perceptible feedback to guide a surgical tool during preparation of a bone to receive the first implant component and the second implant component.

2. The method of claim 1 wherein the representation of the implant component is automatically aligned to fit the plurality of areas representing cartilage.

3. The method of claim 1 wherein generating the plurality of areas representing cartilage comprises:
   transforming the predetermined number of control points to a coordinate space of the representation of the bone; and
   transforming the plurality of cartilage points to the coordinate space of the representation of the bone.

4. The method of claim 3 wherein generating the plurality of areas representing cartilage comprises, for each area representing cartilage from the plurality of areas:
   calculating a distance between a point of the representation of the bone and an associated transformed cartilage point;
   calculating a direction between a closest point of the representation of the bone to an associated transformed control point;
   determining a plurality of points of the representation of the bone that are within a second distance from the associated transformed control point; and
   adjusting the plurality of points based on the second distance and direction to form the plurality of areas representing cartilage.

5. The method of claim 4 wherein each of the plurality of points of the representation of the bone corresponds to a set of polygons from a superset of polygons, the representation of the bone comprising the superset of polygons.

6. The method of claim 5 wherein adjusting comprises adjusting a vertex of each polygon from the set of polygons.

7. The method of claim 5 wherein the superset of polygons comprises triangles.

8. The method of claim 4 wherein calculating the distance between the point of the representation of the bone and the associated transformed cartilage point comprises selecting a closest point of the representation of the bone to the associated transformed cartilage point.

9. The method of claim 3 further comprising, for each area representing cartilage of the plurality of areas representing cartilage, registering a control point from the transformed predetermined number of control points to a closest point in the area representing cartilage.

10. The method of claim 9, wherein the registered control point is constrained to automatically adjust a position of the representation of the implant component.

11. The method of claim 1 further comprising:
    displaying the representation of the bone; and
    displaying the representation of the implant component with respect to the representation of the bone.

12. The method of claim 11 further comprising:
    displaying a representation of a second implant component, wherein the implant component and the second implant component are components of a multiple component implant.

13. The method of claim 12 further comprising determining if a positioning of the representation of the second implant component violates at least one positioning constraint.

14. The method of claim 13 wherein the at least one positioning constraint is based on the representation of the bone, the representation of the implant component, or any combination thereof.

15. A surgical planning system comprising:
a computer programmed to:
  determine a predetermined number of control points for generating a predetermined number of areas representing cartilage, wherein the predetermined number of control points are associated with specified locations on a first implant component of a multiple-component implant; and
a probe configured to measure a plurality of cartilage points, wherein each cartilage point is based on an associated control point from the predetermined number of control points;
wherein the computer is further programmed to:
  generate a plurality of areas representing cartilage based on and in proximity to each cartilage point, wherein each area representing cartilage is associated with a control point, and wherein each area representing cartilage is larger than and projects to an associated control point from the predetermined of control points; and
  select a properly-sized multiple-component implant by computing a distance between two or more measured cartilage points and selecting a multiple-component implant having a distance between the two or more associated control points of the first implant that best matches the computed distance between the two or more cartilage points;
  position a representation of a first implant component of the properly-sized multiple-component implant by aligning the control points for the first implant with the associated measured cartilage points;
  automatically position a representation of a second implant component of the properly-sized multiple-component implant based on the position of the representation of the first implant component; and
  generate at least one virtual cutting boundary based on the position of the representation of a first implant component and the position of the representation of the second implant component, wherein the virtual cutting boundary is configured to provide perceptible feedback to guide a surgical tool during preparation of a bone to receive the first implant component and the second implant component.

16. The surgical planning system of claim 15 wherein the computer is further configured to generate a display of a second implant component, wherein the implant component and second implant component are components of a multiple component implant.

17. The surgical planning system of claim 16 wherein the computer is further configured to determine if a positioning of the representation of the second implant component violates at least one positioning constraint.

18. The surgical planning system of claim 17 wherein the at least one positioning constraint is based on the representation of the bone, the representation of the implant component, or both.

19. The surgical planning system of claim 15 wherein the computer is further configured to generate a user interface that enables a positioning of either the representation of the implant component, the representation of the second implant component, or any combination thereof.

20. A non-transitory tangible computer-readable storage medium having instructions embodied thereon that, when executed by a computing device, cause the computing device to perform operations comprising:
  determining a predetermined number of control points for generating a predetermined number of areas representing cartilage, wherein the predetermined number of control points are associated with specified locations on a first implant component of a multiple-component implant;
  receiving measurements corresponding to a plurality of measured cartilage points, wherein each cartilage point is based on an associated control point from the predetermined number of control points;
  generating a plurality of areas representing cartilage based on and in proximity to each cartilage point, wherein each area representing cartilage is associated with a control point, and wherein each area representing cartilage is larger than and projects to an associated control point from the predetermined number of control points;
  selecting a properly-sized multiple-component implant by computing a distance between two or more measured cartilage points and selecting a multiple-component implant having a distance between the two or more associated control points of the first implant that best matches the computed distance between the two or more cartilage points;
  positioning a representation of a first implant component of the properly-sized multiple-component implant by aligning the control points for the first implant with the associated measured cartilage points;
  automatically positioning a representation of a second implant component of the properly-sized multiple-component implant based on the position of the representation of the first implant component; and
  generating at least one virtual cutting boundary based on the position of the representation of a first implant component and the position of the representation of the second implant component, wherein the virtual cutting boundary is configured to provide perceptible feedback to guide a surgical tool during preparation of a bone to receive the first implant component and the second implant component.

21. A system comprising:
means for determining a predetermined number of control points for generating a predetermined number of areas representing cartilage, wherein the predetermined number of control points are associated with specified locations on a first implant component of a multiple-component implant;
means for receiving measurements corresponding to a plurality of measured cartilage points, wherein each cartilage point is based on an associated control point from the predetermined number of control points;
means for generating a plurality of areas representing cartilage based on and in proximity to each cartilage point, wherein each area representing cartilage is associated with a control point, and wherein each area representing cartilage is larger than and projects to an associated control point from the predetermined number of control points;
means for selecting a properly-sized multiple-component implant by computing a distance between two or more measured cartilage points and selecting a multiple-component implant having a distance between the two or more associated control points of the first implant that best matches the computed distance between the two or more cartilage points;

means for positioning a representation of a first implant component of the properly-sized multiple-component implant by aligning the control points for the first implant with the associated measured cartilage points;

means for automatically positioning a representation of a second implant component of the properly-sized multiple-component implant based on the position of the representation of the first implant component; and means for generating at least one virtual cutting boundary based on the position of the representation of a first implant component and the position of the representation of the second implant component, wherein the virtual cutting boundary is configured to provide perceptible feedback to guide a surgical tool during preparation of a bone to receive the first implant component and the second implant component.

* * * * *